US 008150510B2

(12) United States Patent
Swerdlow

(10) Patent No.: US 8,150,510 B2
(45) Date of Patent: Apr. 3, 2012

(54) SHOCK TIMING TECHNOLOGY

(75) Inventor: Charles Swerdlow, Los Angeles, CA (US)

(73) Assignee: Imperception, Inc., Minneapolis, MN (US)

( * ) Notice: Subject to any disclaimer, the term of this patent is extended or adjusted under 35 U.S.C. 154(b) by 1222 days.

(21) Appl. No.: 11/804,443

(22) Filed: May 18, 2007

(65) Prior Publication Data
US 2008/0033494 A1 Feb. 7, 2008

Related U.S. Application Data

(60) Continuation-in-part of application No. 10/706,793, filed on Nov. 12, 2003, now Pat. No. 7,257,441, which is a division of application No. 10/351,143, filed on Jan. 27, 2003, now Pat. No. 6,675,042.

(60) Provisional application No. 60/372,402, filed on Apr. 15, 2002.

(51) Int. Cl.
*A61N 1/39* (2006.01)
(52) U.S. Cl. .......................................................... 607/7
(58) Field of Classification Search .................... 607/7, 8
See application file for complete search history.

(56) References Cited

U.S. PATENT DOCUMENTS

| | | | |
|---|---|---|---|
| 5,105,809 A | 4/1992 | Bach, Jr. et al. | |
| 5,129,392 A | 7/1992 | Bardy et al. | |
| 5,312,449 A | 5/1994 | Nigam | |
| 5,564,422 A | 10/1996 | Chen | |
| 5,899,929 A | 5/1999 | Thompson et al. | |
| 5,954,753 A | 9/1999 | Alt et al. | |
| 6,052,621 A | 4/2000 | Begemann et al. | |
| 6,246,908 B1 | 6/2001 | Chattipakorn et al. | |
| 6,453,197 B1 | 9/2002 | Parry et al. | |
| 6,675,042 B2 | 1/2004 | Swerdlow | |
| 6,834,204 B2 * | 12/2004 | Ostroff et al. | 607/2 |
| 6,954,672 B1 | 10/2005 | Parry et al. | |
| 6,968,233 B1 | 11/2005 | Parry et al. | |
| 7,257,441 B2 | 8/2007 | Swerdlow | |
| 2004/0215248 A1 | 10/2004 | Hess | |
| 2006/0247687 A1 | 11/2006 | Swerdlow | |
| 2008/0033494 A1 | 2/2008 | Swerdlow | |
| 2008/0051841 A1 | 2/2008 | Swerdlow | |

FOREIGN PATENT DOCUMENTS

EP 536873 4/1993
(Continued)

OTHER PUBLICATIONS

Charles Swerdlow, MD; Kalyanam Shivkumar, MD, PhD; Jianxin Zhang, MS, Determination of the Upper Limit of Vulnerability Using Implantable Cardioverter-Defibrillator Electrograms, Circ. 2003;107:3028-3033.

(Continued)

*Primary Examiner* — George Evanisko
(74) *Attorney, Agent, or Firm* — Skinner and Associates

(57) ABSTRACT

A method for accurately determining timing points for T-wave shocks is particularly useful in a system for determining a cardiac shock strength in an implantable cardioverter defibrillator (ICD. The method involves acquiring at least one first signal, acquiring at least a second signal, comparing the signals, and selecting a timing point with the T-wave of the signal. The first and second signals may be two different aspects of a single electrogram, first and second electrograms, or a combination thereof. Comparison preferably involves signal alignment and qualitative analysis.

43 Claims, 19 Drawing Sheets

FOREIGN PATENT DOCUMENTS

| | | |
|---|---|---|
| WO | WO 98/56461 | 12/1998 |
| WO | WO03089060 | 10/2003 |

OTHER PUBLICATIONS

Charles Swerdlow, MD; Kalyanam Shivkumar and Jianxin Zhang, Determination of the Upper Limit of Vulnerability Using Implantable Cardioverter-Defibrillator Electrograms, DOI: 10.1161/01.CIR. 0000074220.19414.18, Circulation published online Jun 16, 2003.

Paulus F. Kirchhofa, b, C. Larissa Fabritza, b, Markus Zabela and Michael R. Franz, the Vulnerable Period for Low and High Energy T-wave Shocks: Role of Dispersion of Repolarisation and effect of d-sotalol, Cardiovascular Research, 1996 31 (6): 953-962; doi: 10.1016/S0008-6363(96)0058-2.

* cited by examiner

SHOCK TIMING TECHNOLOGY

CROSS-REFERENCE TO RELATED APPLICATIONS, IF ANY

This application is a continuation-in-part of U.S. patent application Ser. No. 10/706,793 filed on Nov. 12, 2003 now U.S. Pat. No. 7,257,441, which is a division of U.S. Regular patent application Ser. No. 10/351,143 filed Jan. 27, 2003 (issued U.S. Pat. No. 6,675,042 on Jan. 6, 2004) which claims the benefit under 35 U.S.C. §119 (e) of U.S. Provisional Patent Application Ser. No. 60/372,402, filed Apr. 15, 2002, which is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to implantable cardioverter defibrillators (ICDs) and defibrillation methods, and particularly to a method and apparatus for determining the optimal shock strength for defibrillation utilizing the upper limit of vulnerability (ULV). More particularly, the invention relates to methods of timing T-wave shocks for purposes of determining cardiac shock strength based on multiple signals within a single electrogram, plural electrograms, or a combination thereof. Most particularly, the invention relates to timing by processing plural signals utilizing qualitative signal measurement techniques and signal alignment techniques.

2. Background Information

Heart disease is a leading cause of death in the United States. The most common form of cardiac death is sudden, caused by cardiac rhythm disturbances (arrhythmias) in the form of a ventricular tachycardia or ventricular fibrillation.

Ventricular tachycardia is an organized arrhythmia originating in the ventricles. It results in cardiac contractions that are too fast or too weak to pump blood effectively. Ventricular fibrillation is a chaotic rhythm disturbance originating in the ventricles that causes uncoordinated cardiac contractions that are incapable of pumping any blood. In both ventricular tachycardia and ventricular fibrillation, the victim will most likely die of "sudden cardiac death" if the normal cardiac rhythm is not reestablished within a few minutes.

Implantable cardioverter defibrillators (ICDs) were developed to prevent sudden cardiac death in high risk patients. In general, an ICD system consists of implanted electrodes and a pulse generator that houses implanted electrical components. The ICD uses implanted electrodes to sense cardiac electrical signals, determine the cardiac rhythm from these sensed signals, and deliver an electrical shock to the heart if life-threatening ventricular tachycardia or ventricular fibrillation is present. This shock must be of sufficient strength to defibrillate the heart by simultaneously depolarizing all or nearly all heart tissue. Shock strength is typically measured as shock energy in Joules (J). The defibrillating shock interrupts the abnormal electrical circuits of ventricular tachycardia or ventricular fibrillation, thereby permitting the patient's underlying normal rhythm to be reestablished. ICD pulse generators are implanted within the patient and connected to the heart through electrodes to provide continuous monitoring and immediate shocking when a life-threatening rhythm disturbance is detected. Because the devices must be small enough for convenient implantation, ICDs are limited in their ability to store electrical energy. In general, ventricular tachycardia can be terminated by weaker shocks than those required to terminate ventricular fibrillation. Thus ICDs must deliver a sufficiently strong shock to insure reliable defibrillation in response to each occurrence of ventricular fibrillation.

It is well known in the art that the shock strength required to defibrillate a human heart effectively varies with the implanted lead configuration and placement as well as the individual heart's responsiveness to the shock. To maximize efficiency of an ICD system, the minimum shock strength necessary to defibrillate an individual patient's heart reliably must be determined. However, it is also well known in the art that the relationship between an ICD's defibrillation shock strength and success or failure of defibrillation is represented by a probability-of-success curve rather than an all-or-none defibrillation threshold (DFT). Very weak, low strength (low energy) shocks never defibrillate. Very strong shocks, at energies greater than the maximum output of ICDs, always defibrillate. However, clinically relevant shock strengths for ICDs lie between these two extremes. In this intermediate range of shock strengths, a shock of a given strength may defibrillate successfully on one attempt and not on another attempt.

Determining a complete curve of the probability of success for every possible shock strength requires many fibrillation-defibrillation episodes. In clinical (human) studies and procedures, the number of fibrillation-defibrillation episodes should be limited because of their associated risks. Thus the goal of testing at the time of ICD implant cannot be to determine a complete probability of success curve. In general, the goal of testing at ICD implant is to provide an accurate estimate of the minimum shock strength that defibrillates with a high probability of success while using a minimum amount of testing. The shock energy that defibrillates with an X % probability of success is referred to as the defibrillation threshold$_X$ or $DFT_X$. Thus a goal of clinical testing at ICD implantation is to estimate a shock strength in the range of the $DFT_{95}$-$DFT_{99}$. This is the optimal strength at which to program the first shock of an ICD. For research purposes, it may be preferable to estimate the $DFT_{50}$.

The minimum measured shock strength that defibrillates during a given session of defibrillation testing is referred to, in general, by the term DFT, despite the fact that no true threshold for defibrillation exists. All methods for determining the DFT of an ICD system require inducing fibrillation a number of times and testing various shock strengths for defibrillation through the implanted defibrillation leads. In the commonly used step-down method defibrillation is attempted at a high shock strength that is likely to defibrillate the heart successfully. If this shock is unsuccessful, a stronger "rescue shock" is delivered to effect defibrillation. Regardless of the outcome of the defibrillation shock, there is a waiting period of about 5 minutes to permit the patient's heart to recover. If the defibrillation shock is successful, fibrillation is reinitiated and the defibrillation is attempted at a lower shock strength. This process is repeated with successively lower defibrillation shock energies until the shock does not defibrillate the heart. The minimum shock strength that defibrillates is the DFT. Depending on the initial shock strength, the DFT determined in this manner is usually between the $DFT_{30}$ and $DFT_{70}$. The ICD is then programmed to a first-shock strength selected to be an estimate of the lowest value that can reliably achieve defibrillation by adding an empirically-determined safety margin to the DFT.

Other methods for determining the DFT require additional fibrillation-defibrillation episodes after a defibrillation shock has failed. In these methods, fibrillation is reinitiated after a failed defibrillation shock and defibrillation is attempted at successively higher shock strengths until a shock defibrillates the heart successfully. This change from a shock strength that does not defibrillate to one that does (or vice versa) is called a reversal of response. DFT methods may require a fixed number of reversals. If the size of the shock increments and decrements is the same, a multiple-reversal (up-down) method provides a good estimate of the $DFT_{50}$. An alternative Bayesian method uses a predetermined number of unequal shock increment steps and decrement steps to estimate an arbitrary, specific point on the DFT probability of success curve.

One significant disadvantage of all DFT methods is the necessity to repeatedly fibrillate and then defibrillate the patient's heart to determine the DFT. A second disadvantage is that successful defibrillation is a probability function of shock energy, not an all or none phenomenon described by a simple threshold.

It is known in the art that shocks delivered during the vulnerable period of the normal cardiac cycle induce ventricular fibrillation, providing that the shock energy is greater than a minimum value and less than a maximum value. The ULV is the shock strength at or above which fibrillation is not induced when a shock is delivered during the vulnerable period of the normal cardiac cycle. The ULV may be displayed graphically as the peak of the vulnerable zone, a bounded region in a two-dimensional space defined by coupling interval (time) on the abscissa and shock strength on the ordinate. The ULV, which can be measured in regular rhythm, corresponds to a shock strength that defibrillates with a high probability of success and correlates strongly with the DFT. Because the ULV can be determined with a single fibrillation-defibrillation episode, it has the potential to provide a patient-specific measure of defibrillation efficacy that requires fewer fibrillation-defibrillation episodes than DFT testing.

Although the vulnerable period occurs generally during the T-wave of the surface electrocardiogram (ECG), its precise timing varies from individual to individual. More importantly, the peak of the vulnerable zone, which corresponds to the most vulnerable time intervals in the cardiac cycle, also varies from individual to individual. Accurate determination of the ULV depends critically delivering a T-wave shock at the peak of the vulnerable zone.

Several methods of determining the defibrillation shock strength for ICDs are based on the ULV. U.S. Pat. No. 6,675,042 ('042 patent) to Swerdlow and Shivkumar, entitled Defibrillation Shock Strength Determination Technology, is incorporated by reference herein.

In one embodiment of the '042 patent, the ULV is determined by shocking the heart at a series of predetermined times in relation to the first temporal derivative of the T-wave and at increasing or decreasing test-shock strengths. The lowest shock strength which fails to induce fibrillation is determined to be the ULV. The optimal first shock strength for programming an ICD is predicted to be incrementally greater than the ULV by about 5 J. In a second embodiment, a vulnerability safety margin method, the heart is shocked at a series of predetermined times in relation to the first temporal derivative of the T-wave, but only at a single test shock energy. If fibrillation is not induced, a safe shock strength is predicted to be incrementally greater than tested shock strength by about 5 J. This safety-margin approach does not determine the minimum (optimal) safe shock strength, but rather only ensures that the programmed shock strength is sufficient. The advantages of the safety margin method are that a sufficient first shock strength for ICDs can be determined without inducing fibrillation and that only three to four test shocks are required. Research has shown that programming first ICD shocks to 5 J above the shock strength tested in this vulnerability safety-margin strategy resulted in a first-shock success rate as good as or better than those reported for other methods of implant testing. Research has also shown that this strategy, which does not require induction of fibrillation, can be applied to at least 80% of ICD recipients.

In another embodiment of the '042 patent, the intra-cardiac electrogram used for determining the derivative of the T-wave is recorded between one (or more) large intra-cardiac electrode(s) such as defibrillation coils and one (or more) extra-cardiac electrodes such as the ICD housing (commonly referred to as a "case" or "can") or the ICD housing coupled to another defibrillation electrode such as a defibrillation coil in the superior vena cava.

One method of the '042 patent is for determining a therapeutic cardiac shock strength for defibrillation, and comprises the steps of:
(a) sensing a change with respect to time in the T-wave of a cardiac signal;
(b) delivering a test shock by:
  (i) delivering a test shock at a test-shock strength and at a test-shock time relating to the change with respect to time of the T-wave; and
  (ii) sensing for cardiac fibrillation; and
(c) if fibrillation is not sensed, repeating step (b) at the test-shock strength and at a different test-shock time relating to the change with respect to time of the T-wave; and
(d) if fibrillation is sensed, setting the therapeutic cardiac shock strength as a function of the test-shock strength.

A particular method for determining an optimal programmed first-shock strength of an ICD relative to the ULV, the ICD having at least one sensing electrode and at least one shocking electrode, comprises the steps of:
(a) setting an initial test-shock strength, four offset times, and a shock strength decrement;
(b) delivering a set of up to four test shocks with the ICD to the patient, each test shock member of the set of test shocks comprising the sub-steps of:
  (i) sensing an electrogram from the patient;
  (ii) detecting at least one predetermined base timing point prior to the T-wave of the electrogram;
  (iii) differentiating the electrogram;
  (iv) detecting at least one maximum of the derivative of a T-wave;
  (v) measuring at least one base time interval from the at least one base timing point to the at least one maximum derivative of a T-wave;
  (vi) delivering a test shock to the patient at the test-shock strength and at a test-shock time corresponding to the base time interval plus one of the offset times;
  (vii) sensing for an induction of fibrillation for a predetermined sensing time period; and
  (viii) if fibrillation is not sensed in step b(vii), then repeating sub-steps b(i-vii), at the same test-shock strength, up to the fourth test shock, each test shock member of the set of test shocks having a different test-shock time corresponding to a base time interval plus an offset time; and (c) if fibrillation is not sensed in step (b) by the fourth test shock, then repeating step (b) at a lower test-shock strength corresponding to the shock strength decrement, to deliver at least one additional set of up to four test shocks; and (d) if fibrillation is sensed in step (b), then:
  (i) defibrillating the patient; and
  (ii) setting the programmed first-shock strength of an ICD at a predetermined higher level than the test-shock strength at which fibrillation was induced.

One embodiment of the apparatus of the '042 patent is an overall ICD system which delivers an optimal therapeutic cardiac shock, comprising:

(a) a plurality of electrodes, at least one electrode being adapted for sensing cardiac signals and at least one electrode being adapted for delivering shocks to the heart;

(b) a shock subsystem connected to the at least one electrode for delivering shocks and which is capable of generating test shocks and therapeutic cardiac shocks; and (c) a ULV subsystem connected to the shock subsystem and for providing test shock information to the shock subsystem, the test shock information including test-shock strength and test-shock time relating to a change in cardiac signals with respect to time, and for determining the shock strength of the therapeutic cardiac shocks as a function of the test shock strength.

Another apparatus embodiment of the '042 patent is a ULV subsystem for determining a therapeutic cardiac shock strength, for example with an existing ICD, comprising:

(a) a sensor for sensing the electrical activity of the heart, including a change with respect to time of the T-wave of a cardiac signal and including the presence of fibrillation;

(b) a test-shock driver for transmitting time and strength information regarding test-shocks;

(c) a controller to determine the cardiac shock strength as a function of the response (fibrillation or no fibrillation) to test-shocks of varying strengths and times.

A particular aspect of the apparatus of the '042 patent is an ICD system for determining and providing an optimal programmed first-shock strength based on the upper limit of vulnerability, comprising:

(a) a plurality of implantable electrodes; and
(b) a shock delivery subsystem for generating and delivering shocks, connected to the electrodes; and
(c) a ULV subsystem comprising;
  i) a sensor, connected to the electrodes, for sensing the electrical activity of the heart, including a change with respect to time of the T-wave of a cardiac signal and including the presence of fibrillation;
  ii) a timer connected to the sensor for providing a series of shock times, timed relative to the maximum derivative of the T-wave;
  iii) a test shock driver, connected to the timer, for transmitting timing and amplitude information regarding T-wave, test shocks;
  iv) a memory unit, connected to the test shock driver and the shock subsystem, for storing programmable values such as pacing cycle length, timing intervals, an initial shock strength, and values for incrementing and decrementing shock strength; and
  iv) a controller, connected to the sensor, test-shock driver, and shock subsystem for incrementally varying shock strength and the shock times, whereby the system provides a test shock having a shock strength and shock time selected by the controller, the shock subsystem delivering an initial test shock to the heart at an initial shock strength and an initial shock time and delivering subsequent test shocks to the heart by varying the shock and decreasing the shock strength, a strength decrement, until the heart is induced to fibrillate, whereby the shock strength of the test shock immediately prior to the test shock that induces fibrillation represents the ULV.

BRIEF SUMMARY OF THE INVENTION

The present invention provides an automatic ICD system and method which is practical, reliable, accurate, and efficient, and which is believed to fulfill the need and to constitute an improvement over the background technology.

The invention provides a method for accurately determining timing points for T-wave shocks is particularly useful in a system for determining a cardiac shock strength in an implantable cardioverter defibrillator (ICD. The method involves acquiring at least one first signal, acquiring at least a second signal, comparing the signals, and selecting a timing point with the T-wave of the signal. The first and second signals may be two different aspects of a single electrogram, first and second electrograms, or a combination thereof. Comparison preferably involves signal alignment and qualitative analysis.

The invention includes an implantable cardioverter defibrillator (ICD) with an optimal shock strength for defibrillation utilizing the upper limit of vulnerability (ULV). The ICD times T-wave shocks for purposes of determining cardiac shock strength based on multiple signals within a single electrogram, plural electrograms, or a combination thereof. Timing is accomplished by processing plural signals utilizing qualitative signal measurement techniques and signal alignment techniques.

Although the embodiments of the invention are for an ICD used for human medical purposes, the multiple signal processing methods, qualitative signal measurement method and signal alignment methods may be used in other devices and fields.

The upper limit of vulnerability (ULV) is the weakest shock that does not induce ventricular fibrillation (VF) in the vulnerable period. It correlates with the defibrillation threshold to permit assessment of ICD defibrillation safety margins without inducing VF in most patients. To determine the ULV, T-wave shocks must time at the most vulnerable interval(s) after the R wave or pacing pulse, corresponding to the strongest shock that induces VF. These intervals are estimated based on timing points selected from multiple surface electrocardiographic leads. To automate the ULV method, these intervals (and hence timing points) must be identified from an ICD electrogram.

The '042 patent describes methods to identifying the optimal timing points for T-wave shocks based on intracardiac electrograms. One of the principal embodiments of this patent requires determining $T_R$, the recovery time. $T_R$ is measured as the maximum of the first derivative of the T-wave. In this embodiment, $T_R$ is the reference timing point for determining timing of T-wave shocks.

The improvements in the present invention relate to signal quality of the sensing electrogram and use of subcutaneous sensing electrodes to select timing points for T-wave shocks. The purpose of these improvements is to improve the accuracy of identifying the optimal timing intervals for T-wave shocks based on intracardiac electrograms.

At times, the maximum value of the first derivative of the electrogram used for measuring $T_R$ occurs during a period in which the signal-to-noise ratio of the sensed electrogram signal is reduced either by signal noise or by the shape of the electrogram. For example, if the maximum value of the first derivative of the far-field electrogram used for measuring $T_R$ occurs during a period in which the shape of the electrogram approximates a straight line segment. Hence the value of the first derivative is approximately constant over period of interest. Because of this, small variations in signal amplitude caused by noise may have a large effect on the measured timing of $T_R$. This may introduce error and limit the accuracy of timing measurements.

ICDs under development may use only subcutaneous sensing and defibrillation electrodes without any intracardiac electrodes. The shape of cardiac electrical signals recorded from subcutaneous electrograms is similar to that of the surface ECG.

The features, benefits and objects of the invention will become clear to those skilled in the art by reference to the following description, claims and drawings.

DETAILED DESCRIPTION

1. Basic Devices and Methods for Determining Defibrillation Shock Strength Utilizing Timed T-wave Shocks The Devices and Methods for Determining Defibrillation Shock Strength Utilizing Timed T-wave Shocks are particularly well suited for use with the Timing Systems, Devices and Method described in Section 2 below.

Figure 1:
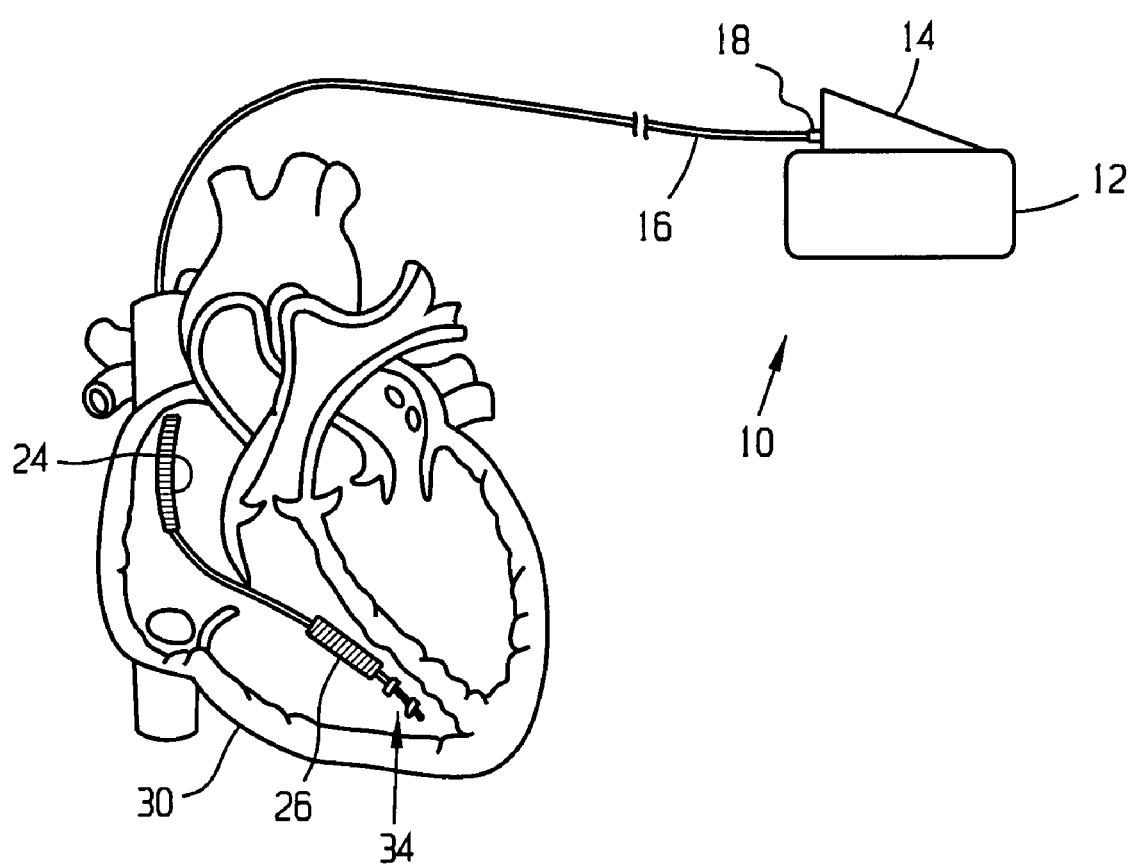
FIG. 1 is an anterior sectional view of a human heart in relative anatomical position, depicting the relative positioning of intravascular electrode catheters and an ICD according to the present invention.

Referring to FIG. 1, an embodiment of the present invention is depicted as an ICD system 10 comprising an implantable electrical pulse generating housing or "can" 12, an electrical connector pin housing 14, an implantable intravascular catheter 16 electrically connected to pin housing 14 via a pin connector 18. Catheter 16 carries proximal defibrillation discharge electrode 24 and distal defibrillation discharge electrode 26, electrodes 24 and 26 sometimes being referred to as "coils", and is configured to position proximal electrode 24 within right atrium 28 and position distal electrode 26 within right ventricle 30. Catheter 16, also carries a set of pacing/sensing electrodes 34 positioned within the right ventricle 30 at the tip of the catheter 16. Alternatively, the high-voltage discharge electrodes 24 and 26 may be disposed on a different catheter than the pace/sense electrode set 34, comprising the ring electrode 35 and tip electrode 36. Further, an additional set of pace/sense electrodes may be used. As yet another alternative, separate electrode pairs may be used for right-ventricular pacing and sensing. The catheters, discharge electrodes and pacing/sensing electrodes may be of any implantable design known to the art (including intracardiac, epicardial, intravascular, subcutaneous or submuscular designs). At least one defibrillation electrode must be intravascular or epicardial, with a preferred embodiment using a pacing electrode and defibrillation electrode near the right ventricular apex. Positioning of implanted pacing electrodes is preferred to be near the right ventricular apex or left ventricle, but is also not critical so long as pacer capture is reliable. This invention also permits determination of ULV without any surface electrodes.

Because DFTs vary with electrode placement and lead configuration, as well as with the responsiveness of a particular patient's heart, the ULV is determined after the electrodes and leads have been placed at their permanent positions. In this manner, the DFT corresponds to the patient and particular arrangement of the defibrillation electrodes used.

Figure 2:
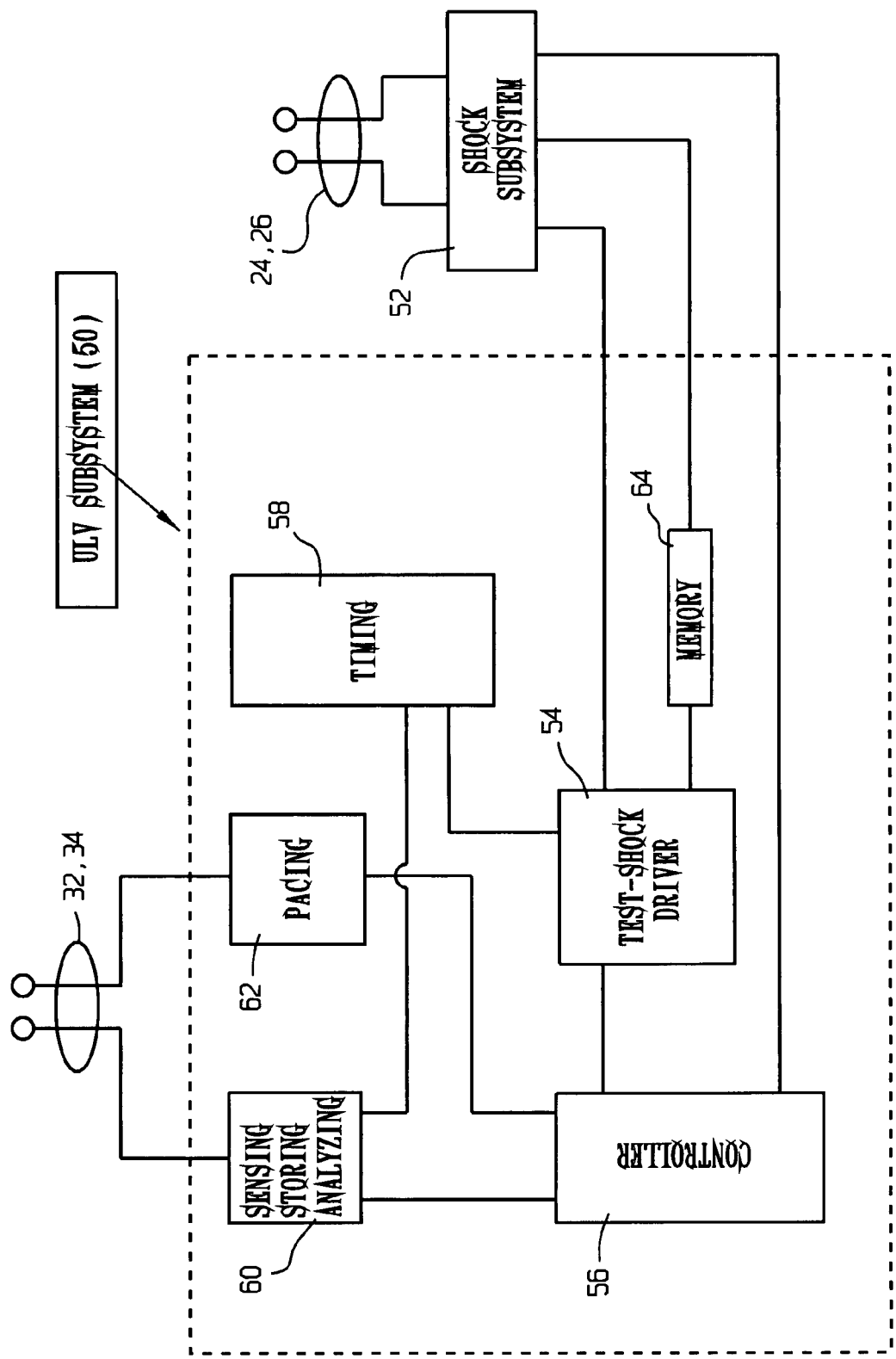
FIG. 2 is a schematic block diagram depicting a suitable arrangement for an ICD according to the present invention.

Referring to FIG. 2, an embodiment of an upper limit of vulnerability (ULV) subsystem 50 according to the present invention is depicted in one possible configuration in electrical connection with a shock subsystem 52. ULV subsystem 50 and shock subsystem 52 are component subsystems of ICD 10 of FIG. 1 and are contained within housing 12 and electrically connected. ULV subsystem 50 includes a test-shock driver for T-wave shocks 54, a test/treatment controller 56, an improved timing circuit or component 58, an improved sensing, storing, and comparing circuit or component 60, a pacing circuit or component 62 (in a preferred embodiment), and a memory unit or component 64. Shock subsystem 52 may be of any design known to the art, but preferably is programmable to deliver either monophasic or biphasic shocks, having variable tilt, and controllable through a stepwise range of energy outputs from at least 5 J to at least 30 J. Shock subsystem 52 is preferably connected to the test shock driver 54, memory 64 and controller 56 of the ULV subsystem 50. Shock subsystem 52 is used to deliver test shocks as well as defibrillation shocks. The pacing circuit 62 is not necessary for embodiments of the method and system which are operative in a native rhythm. Other apparatus may be used to apply the system of using plural signals to improve T-wave shock timing.

Figure 3:
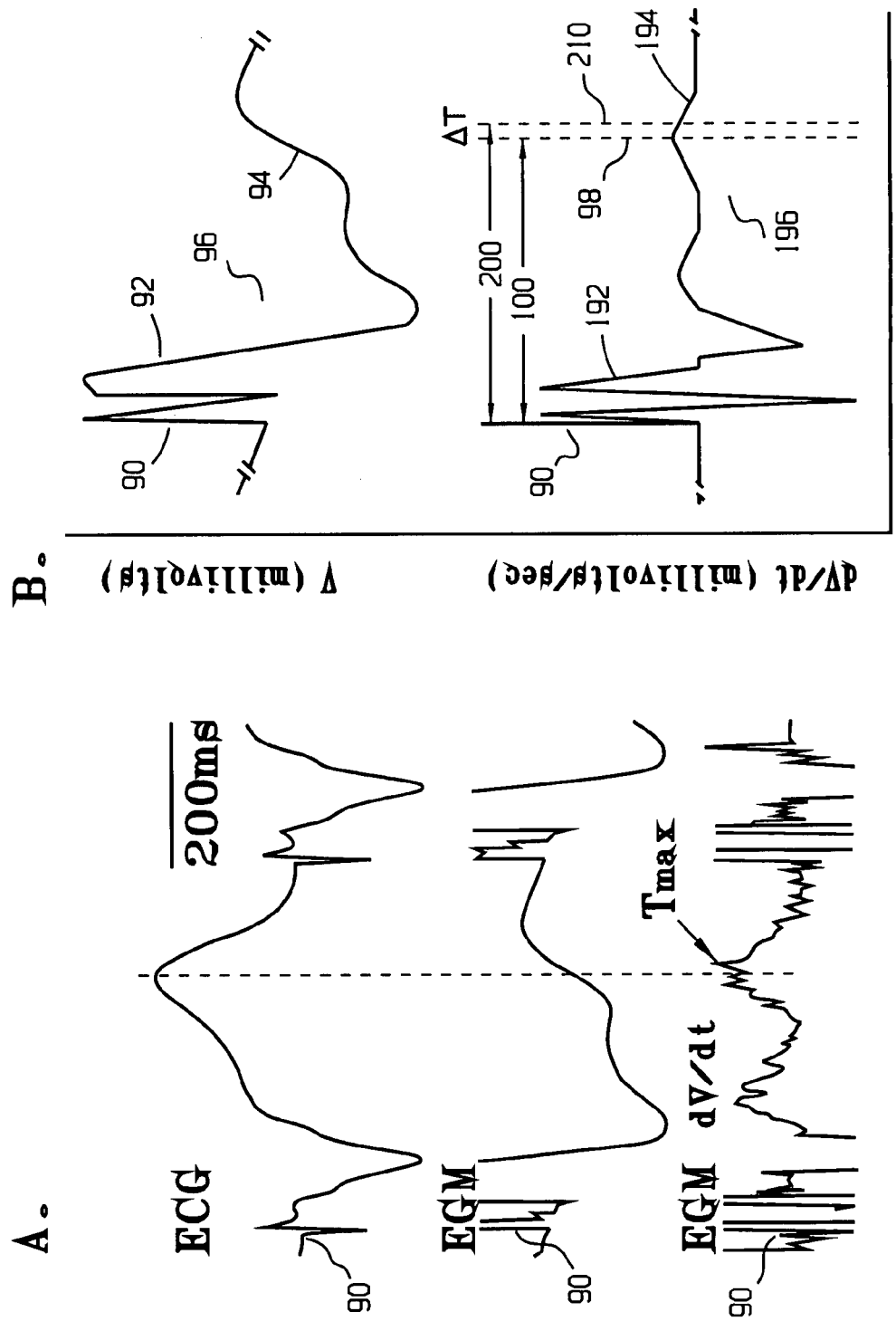
FIG. 3A. is a Prior Art actual recording of ECG lead II, an intracardiac electrogram (EGM), and its first time derivative (EGM dV/dt).
FIG. 3B is a Prior Art timing diagram that represents an expanded version of the lower two panels in FIG. 3A. It depicts the relationship between a paced cardiac cycle and test electrical shocks in accordance with a preferred embodiment of the present invention. The upper panel in FIG. 3B depicts an intra-cardiac electrogram, and the lower panel depicts its first time derivative.
Figure 4:
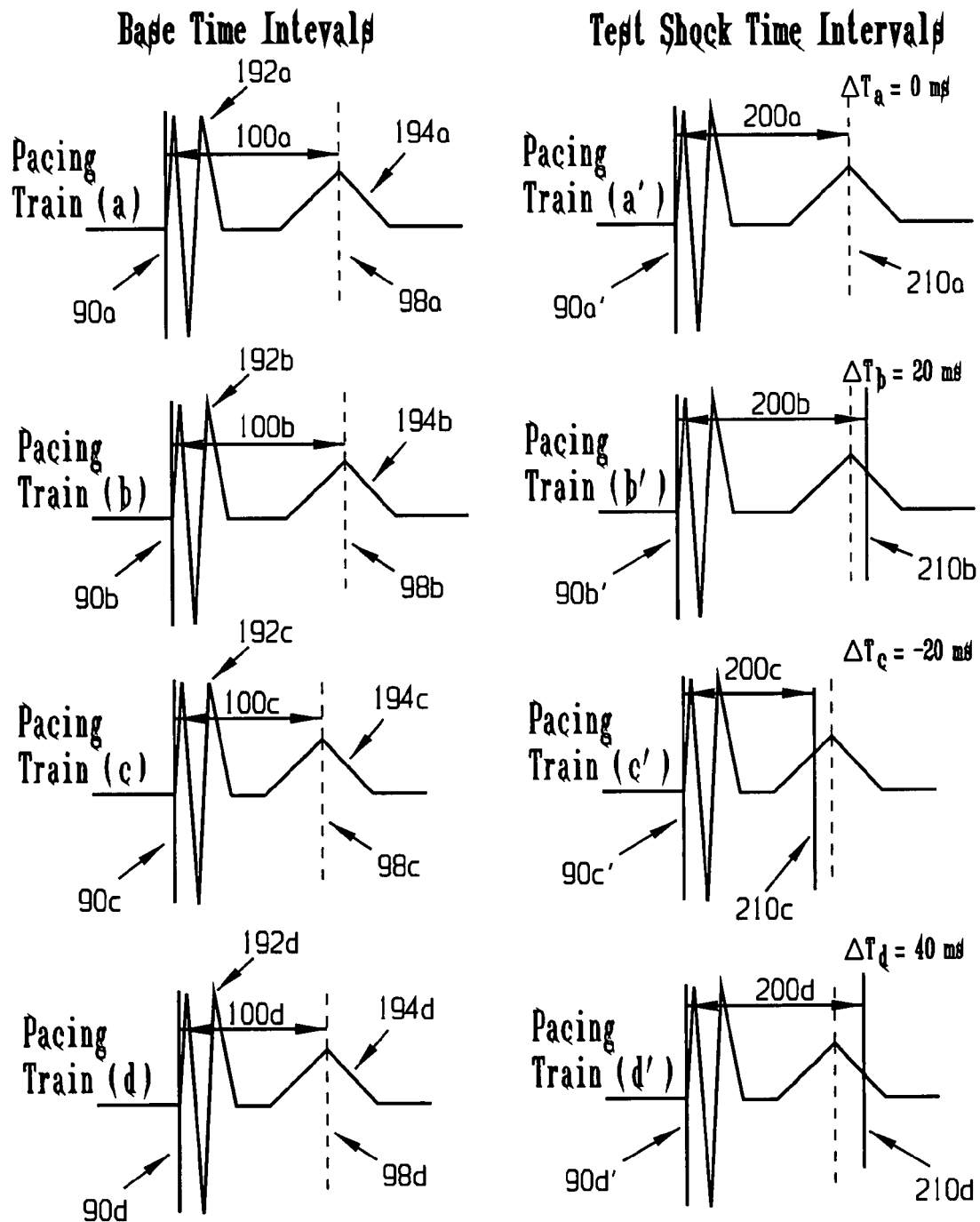
FIG. 4 is a Prior Art diagram illustrating how the timing of test shocks is determined from the derivatives of an intracardiac electrogram for a sequence of test shocks at a single shock energy in accordance with an embodiment of the invention. Each row displays the timing measurement and corresponding shock delivery time for a single test shock.

The operation of the overall system 10 of determining shock strength, which utilizes the system and method of improved T-wave shock timing of the present invention, is described in reference also to FIGS. 3B and 4. System 10 is an embodiment of the invention which utilizes pacing. The system can be modified to operate in a native rhythm as described below. Controller 56 is set to test, providing a starting test-shock strength (also called a shock-strength value or energy level), and triggering sensing circuit 60. This sensing circuit 60 detects the heart's intrinsic rate and transmits this rate value back to controller 56. The starting shock strength is stored in memory unit 64. The intrinsic heart rate value is passed to pacing circuit 62. Pacing circuit 62 then provides a baseline pacing output through to electrode set 34 that is of a rate sufficient to overdrive the heart's intrinsic rate. Referring to FIG. 3B, the sensing, storing, and comparing circuit 60 then evaluates the intra-cardiac electrogram 96, which represents the electrical activity of the heart, for the presence of a QRS complex 92, the T-wave 94, a change with respect to time in the entire electrogram 196, for example the derivative of the QRS complex 192, and derivative of the T-wave 194.

The timing of the pacer spike 90 may be transmitted to the sensing circuit 60 electronically by methods well known in the art. Alternatively, the sensing, storing, and comparing circuit 60 may identify the pacer spike 90 during its evaluation of the intra-cardiac electrogram. The present invention anticipates an ability to evaluate the ECG or electrogram signals derived from a number of different configurations of implanted electrodes including, but not limited to, intracardiac, epicardial, intravascular, subcutaneous, and submuscular leads. Examples of sensing lead combinations may include leads positioned to record signals from the superior vena cava, the right atrium, the right ventricle, the left ventricle and combinations of electrodes such as between a lead tip electrode and a defibrillation electrode or combinations including pairing leads from the right atrium or the superior vena cava to the right or left ventricles.

Ventricular pacing is performed at a predetermined cycle length, such as 500 ms, for a predetermined duration such as 8-15 beats. The sensing and storage circuit 60 evaluates the T-waves and their time derivatives from the combinations of implanted electrodes provided during said ventricular pacing. It uses one of several algorithms for selecting a lead for timing purposes. One such algorithm is to select the lead in which the derivative of the T-wave has the latest peak.

Referring to FIG. 3A, the single electrogram was recorded between right-ventricular coil and left-pectoral case plus a superior vena cava electrode. The method in the "042" patent selects the peak 98 of a signal representing a change with respect to time of the T-wave, for example the derivative of the T-wave 194 for timing purposes.

Referring to FIG. 3B, the base time interval 100 is measured between the pacer spike 90 and the maximum (peak) 98 of the derivative of the T-wave 194. The test shock is delivered at time 210, offset from a change with respect to time in the T-wave of a cardiac signal (as is also discussed in the Summary), preferably the maximum of the derivative of a T-wave, by time $\Delta T$, and corresponding to time interval 200 after the pacer spike 90. Offset time ($\Delta T$) is defined in general as the difference between the time of the test shock ($T_{shock}$) and the time of maximum or peak of the relevant cardiac electrical signal ($T_{max}$). In the preferred embodiments, $T_{max}$ represents either the maximum of the time derivative of the T-wave or the peak of the latest-peaking monophasic T-wave that is opposite in polarity to the QRS complex or some combination thereof. A negative value of $\Delta T$ indicates a time preceding the peak. A positive value indicates a time after the peak.

Referring to FIG. 4, the left column indicates determination of four successive base time intervals 100a-d, corresponding to four different pacing sequences or trains (a)-(d). The right column indicates how these base time intervals are used to select the time intervals 200a-d of four successive test shocks at the same shock energy, delivered relative to corresponding pacing trains (a')-(d'), which may be the trains as (a)-(d) or different trains. Dashed vertical lines in both columns coincide with the maxima 98a-d of the derivatives of the T-wave. Continuous vertical lines in the right column correspond to the shock time points. In each row, the base time intervals 100a-d on the left are added to the corresponding stored values for offset times $\Delta$Ta-d to calculate the shock-time intervals 200a-d, corresponding to test shock times 210a-d.

The timing circuit 58 first determines a base time interval 100a measured from the pacer spike 90a to the maximum 98a of the derivative of the T-wave 194a. The base time intervals 100a-d may be measured on one or more beats preceding the last beat of the same train of pacing pulses as the test shock. Alternatively, it may be measured on an immediately-preceding train of pacing pulses as mentioned previously. These base time intervals may be measured on a single beat or may represent the average of several beats. In one embodiment, pacing trains (a) and (a') are the same, as are (b) and (b'), (c) and (c'), and (d) and (d'). Then in FIG. 4 each row corresponds to the last two beats of successive pacing trains (a)-(d). Base time intervals 100a-d may be measured on the next to last beats of the pacing trains (following pacer spikes 90a-d), and test shocks delivered into the T-wave of the last beats of the train (following pacer spikes 90a'-d').

In one embodiment, the baseline time intervals 100a-d are measured on both the preceding pacing train (using either a single-beat or average-of-several beats) and on the current pacing train, corresponding to each of the four rows in FIG. 4, using the last beat prior to the test shock. The test shock is aborted if the difference between these two measurements is greater than a predetermined value in the range of 1-40 ms, preferably 5-20 ms, and most preferably 10 ms. This prevents delivery of test shocks in the event that the pacing train does not result in consistent capture (due to supraventricular capture beats, premature ventricular beats, or loss of capture) or the peak of the time derivative of the T-wave 194 a-d is not measured consistently.

The first or starting shock-strength value and a first offset time ($\Delta$Ta) are stored in memory unit 64 and are transmitted to test-shock driver 54. The test-shock driver 54 triggers shock subsystem 52 to deliver a first test shock with the starting shock strength at a first shock time point 210a, which occurs at first time interval 200*a* after the next pacing spike 90*a'*. First time interval 200*a*, determined by timing circuit 58, is calculated by adding the first offset time ΔTa to the previously measured base time interval 100*a*. In FIG. 5 $T_{max}$ refers to the maxima 98*a-d* of the derivatives of the T-waves 194*a-d*. In an alternative embodiment, it may refer to the peak of a monophasic T-wave.

Note that the base time interval 100 shortens between pacing trains (b) and (d), but the offset times $\Delta T_{a-d}$ remain fixed relative to the maxima of the derivatives 98*a-d*.

The starting shock strength and offset time ΔTa-d are stored in memory unit 64 and are chosen according to a predetermined protocol. The starting shock strength is in the range of 5-30 J, preferably between 10-15 J, and most preferably 15 J. Offset time ΔT may be positive, negative or zero. Offset time ranges between negative (−) 60 ms and positive (+) 40 ms and is preferably −20 ms to +40 ms for a standard three-electrode defibrillation configuration (right-ventricle to case plus superior vena cava). At least one offset time is stored and preferably four (4) in the preferred embodiment. The initial value of offset time ΔT is preferably about 0 ms whereby the initial test shock is delivered such that it substantially coincides with the maximum of the derivative of the T-wave following the next pacer spike 90*a'*.

In an alternative normal-rhythm embodiment of the apparatus, time delays are calculated in a similar fashion, except that they are based on measurements made in normal rhythm. A time interval is calculated based on the interval between the detected QRS complex (as opposed to a pacer spike) and the peak of the time derivative of the selected intra-cardiac T-wave.

The sensing, storing and comparing circuit or component 60 most preferably selects timing points based on at least two different types of signals from a single electrogram, a single type of signal from at least two electrograms, or a combination of these two plural signals, as discussed below.

In most cases, the initial test shock energy is sufficiently strong such that fibrillation is not induced. After delivery of the first test shock, pacing from the pacing circuit 62 is turned off and the cardiac rhythm is monitored by the sensing storing and comparing circuit 60 for the presence of fibrillation.

If fibrillation is not induced by the first test shock, controller 56 waits a predetermined period of time, preferably about one (1) minute, before starting the next test shock. During this and all subsequent waiting periods, a pacing train (in this case train (b)) may be delivered and analyzed by sensing and storage circuit 60. This analysis updates interval 100 based on the timing of the maximum of the derivative of the intra-cardiac T-wave. This updated interval 100 is stored in timing circuit 58 for the next test-shock pacing sequence. Alternatively, sensing and storage circuit 60 may analyze the timing of the maximum of the derivative of the intra-cardiac T-wave during the paced beats of each pacing train and that value may be used to determine the timing of the shock at the end of the same pacing train. In this case, no pacing train is delivered during the waiting period, and the value of interval 100 is not updated until the waiting period ends and the test-shock's pacing train begins. In either case, these additional measurements result in updated measurements 100*b-d* of the base time interval 100 for each successive test shock in the sequence as shown in FIG. 4.

After the first test shock and monitoring and waiting period, controller 56, is programmed to deliver up to three additional sequences (a total of four) of ventricular pacing at a predetermined cycle length for a predetermined number of beats followed by test shocks at the same starting shock strength (a total of four test shocks), at different intervals 200*b-d* corresponding to times 210*b-d*, followed by additional monitoring and waiting periods.

For the second test shock in the first round of test shocks, timing circuit 58 determines a second time interval 200*b* from the pacer spike 90*b*, corresponding to the base time interval 100*b* plus a second ΔTb 210*b* which is preferably plus 20 ms. The heart is shocked at the end of this interval 200*b*, which occurs at second shock time point 200*b*, which falls 20 ms after the maximum derivative 98*b* of the T-wave 194*b*.

If fibrillation is not induced, the controller 56 waits the predetermined wait period before initializing the chain of events leading to the third test shock at the first shock strength and commences with timing circuit 58 determining a third time interval 200*c* from pacer spike 90*c* corresponding to base time interval 100*c* plus third ΔTc which is preferably minus 20 ms. The heart is shocked at the end of this interval 200*c*, which occurs at third time point 210*c* which is preferably 20 ms before maximum derivative 98*c* of the T-wave 194*c* and the heart is shocked again.

If fibrillation is not induced by the third test shock, the controller 56 waits the predetermined wait period before initializing the chain of events that results in a fourth test shock at the first shock strength. Timing circuit 58 determines a time interval 200*d* from pacing spike 90*d* corresponding to the base interval 100 plus a fourth ΔTd which is preferably plus 40 ms. The resultant shock time point 210*d* that is preferably 40 ms after the maximum 98*d* derivative of the T-wave 194*d*. After each test shock the cardiac rhythm is monitored by the sensing circuit 60 to ascertain if the shock has induced fibrillation. If fibrillation is not induced, the controller 56 waits the predetermined wait period before delivering the next test shock.

In the example shown in FIG. 4, base time interval 100 shortens between the times of the second and third rows so that base intervals 100*c* and 100*d* are shorter than base intervals 100*a* and 100*b*. Similarly, shock timing intervals 200*c* and 200*d* are shorter than shock timing intervals 200*a* and 200*b*. However, the offset intervals ΔTc and ΔTd remain appropriately timed relative to the peaks of their corresponding derivatives 194*c* and 194*d*. Although this illustration shows only one change in base time interval 100, any change in this base time interval is accompanied by a corresponding change in the shock-time interval 200.

If fibrillation is not induced by a series of four T-wave shocks at the same shock strength shock and different intervals 200*a-d*, controller 56 lowers the shock strength by a predetermined test-shock strength decrement value which is also stored in memory unit 64 and set by a predetermined protocol. The controller 56 waits the predetermined wait period before transmitting the newly determined, second test-shock strength to the test-shock driver 54 and then to shock subsystem 52 after the predetermined waiting period. This initiates a second series of up to four test shocks. The first test shock in the second round is delivered at a first time point corresponding to a first timing interval determined by timing circuit 58 after a pacing spike 90. Preferably, all of the time offsets ΔT in the second round are equivalent to those in the first test shock sequence. However, one or more of the time offsets may be varied. The amount by which the second test-shock strength is reduced relative to the first shock strength (i.e. the shock energy decrement value) is in the range of 1-10 J, usually in the range of 2-5 J. The preferred decrement value is about 5 J at test-shock strengths of 10 J or greater and about 2 J at test-shock strengths of about 5 J or less. The specific values may be selected from one of various testing strategies, including those used for selecting shock decrement values for DFT testing. The sequence of test shocks in the second sequence is repeated in the same manner as that described with respect to the starting sequence until fibrillation is induced.

If fibrillation has not been induced after the second round of test shocks, one or more subsequent rounds of test shocks may be administered until the system minimum level shock strength, typically 2 J-5 J, is reached. Each subsequent round preferably has the same maximum number of test shocks, each delivered at the same corresponding time offsets $\Delta T$ relative to the end of time interval 100, which is updated prior to each test shock. The test-shock strength of the next round is determined by lowering the shock strength of the previous round by a decrement value that in general is specific to the shock value corresponding to the previous round. Therefore, in this embodiment, for each test-shock strength, there is a set of up to four test-shocks, corresponding to each of the four shock time points 210*a-d*, calculated by adding an offset times $\Delta Ta-d$ to base time intervals 100*a-d*. In a preferred embodiment, time intervals 200*a-d* are calculated based on electrogram measurements made in paced rhythm.

If a test shock in any shock sequence induces fibrillation then the shock strength of the last shock sequence in which no shock induced fibrillation (i.e. the shock strength of the prior shock sequence) may be accepted as the step-down ULV (which is an accurate estimate of the DFT). If fibrillation has not been induced even at the system minimum, 1-5 J level as determined in step 85, the ULV is calculated to be the minimum tested shock strength in step 87; and the defibrillation shock strength is set to a level incrementally above the ULV, preferably with an increment of at least 5 J.

In the safety-margin embodiment referred to previously, testing is limited to the first round or sequence of four shocks at a single shock strength if fibrillation is not induced. No second or subsequent round is utilized. The first ICD shock is then programmed incrementally above this value.

As was discussed above, in most cases the initial test shock energy is sufficiently strong such that fibrillation is not induced. The present invention anticipates that a small fraction of patients will fibrillate in response to the first shock strength. Referring to FIG. 5, this condition is identified in step 89. If this occurs, the test-shock strength is incremented to a next higher shock strength in step 70 based on data stored in memory 72 and testing is repeated. As noted above, this testing consists of pacing the heart for a predetermined number of beats, delivering a shock at a predetermined time interval after the last pacer spike, observing for the induction of fibrillation, and if fibrillation is not induced iterating this process at up to three other time intervals. If fibrillation is not induced by any shock at this higher shock strength, step 89*a* determines that fibrillation has been induced at least once. Step 89*b* then determines if the present shock is the last shock in a four-shock sequence. If it is, the ULV is set equal to this value in step 87. If the present shock is not the last shock in a four-shock sequence, step 89*b* continues the testing sequence.

If fibrillation is induced, step 85*b* again determines if the present shock value equals the system maximum shock strength. If it does not, waiting period 83 is reinitiated, counter 84 is reset to 1, and the shock strength is incremented to the next higher value in step 70 based on data stored in memory 72. The testing process is iterated until a shock strength is reached at which fibrillation is not induced by any of four test shocks as determined by step 89*b*. This shock strength is set equal to the ULV in step 87. If test shocks at the maximum system energy induce fibrillation, the ULV is determined to be greater than this value in step 88*b*. In this case, the ICD system usually is revised by changing electrodes, shock waveform or polarity, maximum system energy, or some other parameter.

Alternative embodiments may provide more accurate estimates of a shock strength associated with a specific probability of defibrillation success, but they require additional fibrillation-defibrillation episodes. These involve the concept of multiple reversals between shock strength that do not induce fibrillation and those that do induce fibrillation analogous to the reversal of response methods for determining the DFT. Methods that utilize a specific number of equal-size reversal steps or a Bayesian method for selecting unequal steps can be applied to ULV testing as well as to DFT testing. They provide a more accurate estimate of a specific point of the defibrillation probability of success curve.

In one embodiment, the baseline time intervals 100*a-d* are measured on both the preceding pacing train (using either a single-beat or average-of-several beats) and on the current pacing train, corresponding to each of the four rows in FIG. 5, using the last beat prior to the test shock. The test shock is aborted if the difference between these two measurements is greater than a predetermined value in the range of 1-40 ms, preferably 5-20 ms, and most preferably 10 ms. This prevents delivery of test shocks in the event that the pacing train does not result in consistent capture (due to supraventricular capture beats, premature ventricular beats, loss of capture) or the peak of the time derivative of the T-wave 194*a-d* is not measured consistently.

While the above embodiments are implemented in an ICD, the invention can also be implemented in an ICD programmer or an independent external device for testing defibrillation efficacy. Such a device may be referred to as "an implant-support device."

When the invention is implemented in a programmer or implant-support device, surface ECG leads, one or more electrograms including the electrogram that is differentiated, and the differentiated signal may be displayed on a computer screen to be viewed by an operator. The timing points 90*a-d*, and 98*a-d* and timing intervals 100*a-d* may also be displayed on the computer screen. In one embodiment test shocks are not delivered unless the operator confirms the automatically-selected timing points and intervals. The operator may alter the timing points and intervals manually using an input device such as a mouse, trackball, touch-screen pen, or other such input devices that are well known in the art. This operator-assisted method of selecting timing points and intervals may also be used with an ICD. In this embodiment, the electrograms, differentiated electrograms, timing points and timing intervals are sent from the ICD to the programmer via telemetry, and the programmer telemeters the confirmation signal or modifications of the timing points and intervals to the ICD prior to delivery of the test shock. In these operator-assisted embodiments, the baseline time intervals 100*a-d* are measured on one preceding pacing train and the test shocks are delivered on a subsequent pacing train.

Figure 5A:
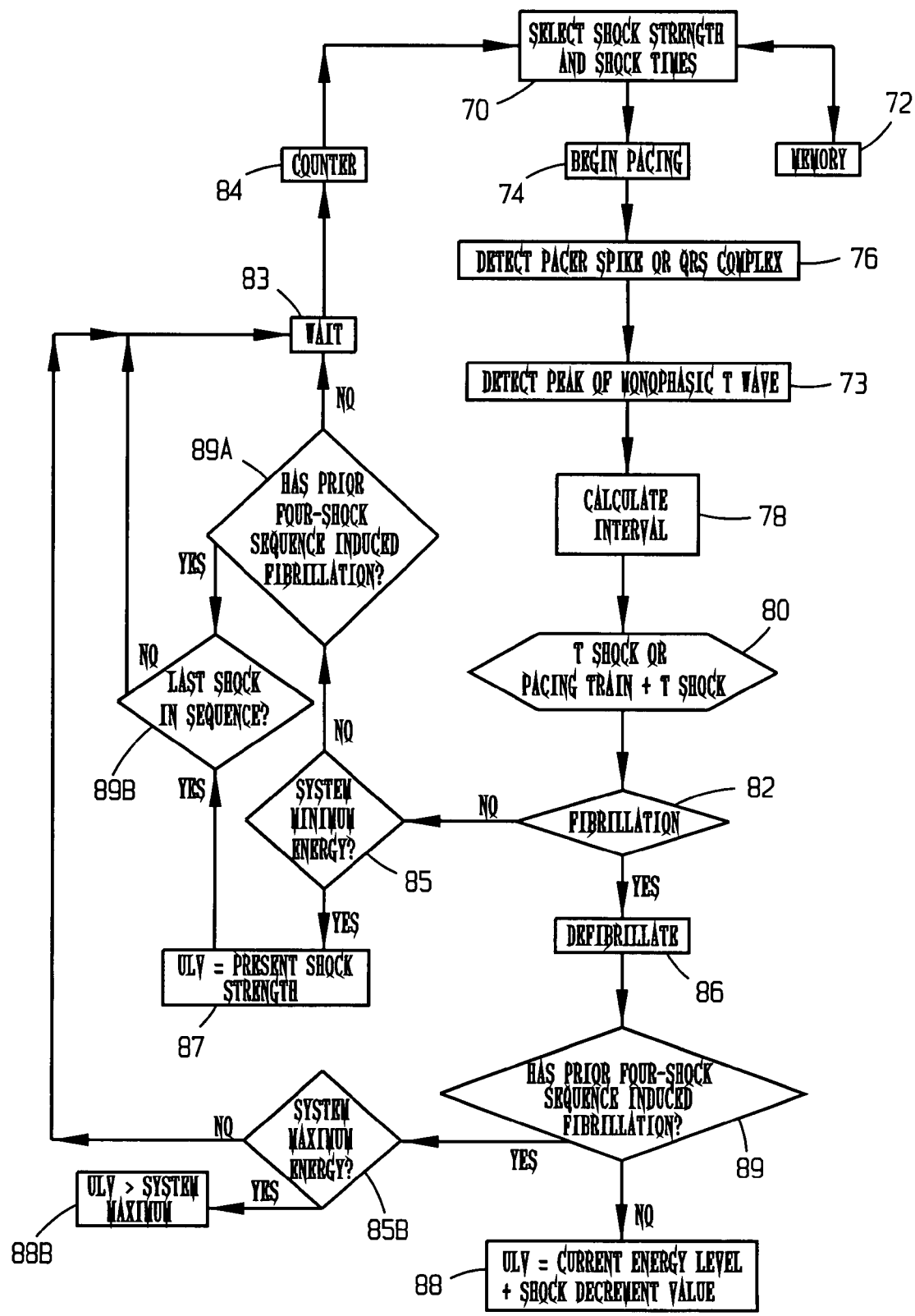
FIG. 5 is a block diagram depicting a Prior Art sequence of steps for determining shock strength based on T-wave shock timing, which utilizes the methods of this invention.

Referring also to FIG. 5A, a preferred embodiment of the method of determining the optimal shock strength for defibrillation utilizing the upper limit of vulnerability (ULV) with improved timing of T-wave shocks begins with step 72 wherein a first or starting test-shock strength, one or more offset time intervals ($\Delta T$), and one or more test-shock strength decrement value(s) are stored in and retrieved from memory unit 64 of the ULV subsystem 50. The starting shock strength, shock decrement value, and offset times $\Delta T$ are chosen according to a predetermined protocol. As was discussed above with respect to the apparatus of the invention, the preferred first shock strength is in the range of 10-15 J, but may range from 5 J to 30 J. The preferred number of shocks is four (4). Therefore, in this embodiment, for each test-shock strength there is a set of up to four test shocks corresponding to each of the four shock time points $210a$-$d$. Each test-shock time $210a$-$d$, falls at the end of time intervals $200a$-$d$, after a respective pacing spikes $90a$-$d'$. The time intervals $210a$-$d$, $210b$, $210c$ and $210d$ are calculated by adding an offset times $\Delta Ta$-$d$ to base time intervals $100a$-$d$. The base time $100a$-$d$ is the time between the pacing spike $90a$-$d$ to the maximum derivative of the T-wave $194a$-$d$ in the electrogram $192a$-$d$ proceeding electrograms $192a$-$d$. In a one embodiment of the invention, time intervals $200a$-$d$ are calculated based on electrogram measurements made in paced rhythm.

However, these shock-time intervals may alternatively be based on measurements made in normal rhythm as described below. In the one embodiment, step 74 initiates overdrive pacing of the heart. One method for selecting intervals in paced rhythm is shown in step 73. This method may be applied only if a recorded electrogram has a suitable monophasic T-wave.

In step 76, pacing is confirmed and a pacer spike is detected or one or more QRS complexes are detected and electrograms are recorded. In step 73, the peak of the latest peaking monophasic T-wave of the one or more QRS complexes is identified by analyzing electrogram morphology in each recorded lead. The next step is to select time intervals 78.

Figure 5B:
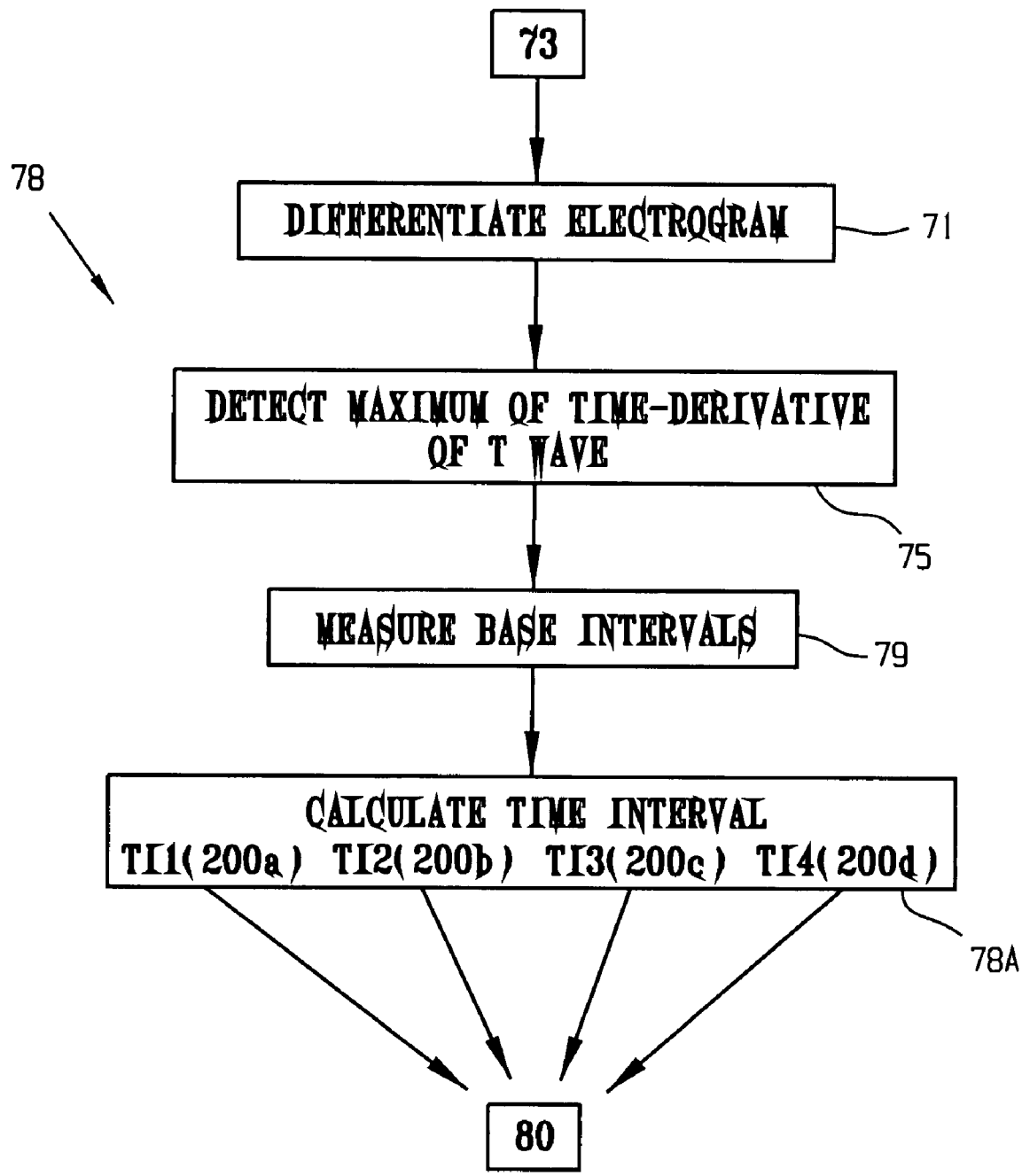

Referring to FIG. 5B, the method of the '042 patent for selecting time intervals 78' for a single electrogram in paced rhythm is shown in steps 71, 75, and 77. This method can be applied regardless of whether a monophasic T-wave is present. In step 71, the electrograms recorded and analyzed in step 76 are differentiated with respect to time. In step 75, the maximum of the time derivative of the T-wave is determined from the first time derivative of each electrogram $196a$, the latest of these peaks $98a$ is selected, and base time $100a$ is calculated from the pacer spike $90a$ to such peak $98a$. In step 78, a shock-time interval $200a$ is calculated by adding one of a predetermined time offset intervals $\Delta T$ stored in step 72 to the base interval $100a$ determined in step 75. $\Delta T$ may be positive, negative, or zero. Offset time $\Delta T$ ranges between negative (−) 60 ms and positive (+) 40 ms and is preferably −40 ms to +20 ms. The initial $\Delta Ta$ is preferably about 0 ms. In the preferred embodiment, first time interval $200a$ is calculated based on $\Delta Ta$ of 0 ms. It starts at the time of pacing spike $90a'$ and ends at shock-time point $210a$, which occurs substantially simultaneously with the latest maximum peak of the derivative of the T-wave. As FIG. 3A shows, it is also substantially simultaneous with the peak of the latest-peaking monophasic T-wave on the surface ECG. In subsequent cycles of step 78, where applicable, second, third and fourth intervals may be calculated. Second time interval $200b$ is based on $\Delta Tb$ of +20 ms and begins at pacer spike $90b$ and yields shock time point $210b$ which is approximately 20 ms after the maximum $98b$ of the derivative of the T-wave $194b$. Third time interval $200c$ is based on $\Delta Tc$ of −20 ms, begins at pacer spike $90c$ and yields third time point $210c$ which is about 20 ms before the maximum $98c$ of the derivative of the T-wave $194c$. The fourth interval $200d$ is based on $\Delta Td$ of +40 ms, begins at pacer spike $90d$ and yields fourth shock time point $210d$ which is about 40 ms after the maximum $98d$ of the derivative of the T-wave $194d$.

Then after the next suitable pacer spike $90a'$, step 80 initiates a first test shock which is delivered to the heart after first interval $200a$ calculated in step 78. Following first test shock, pacing is turned off in the embodiment utilizing pacing, and the heart is monitored for the induction of fibrillation at step 82. As was discussed above in connection with the apparatus of the invention, in most cases, the initial test shock energy is sufficiently high such that fibrillation is not induced. If no fibrillation is detected, step 83 involves waiting a predetermined period of time of approximately one (1) minute, and a counter is incremented at step 84. Subsequently, the process is repeated beginning at selection step 70 selecting the next offset time T and utilizing the same (first) shock strength. The process may be repeated up to a predetermined maximum number of shocks, preferably four (4), in a round or sequence, at the first test-shock strength. Since the first shock strength is selected such that it is too high to induce fibrillation in most patients, usually a second sequence or round of one or more test shocks up to the predetermined maximum number per round will be initiated, at preferably the same shock-time delays, but at a lower shock strength.

After the first sequence of a preselected number of test shocks at the same energy, the counter has reached the predetermined maximum, in this case four. Then step 84 resets the counter to one. This causes step 70 to determine a new test-shock strength based on adding the predetermined shock decrement value stored in step 72, preferably 5 J, to the existing test-shock strength used in step 70. The second round or sequence of test shocks then delivers shocks in the same manner as that described above with respect to the first sequence. If after the second round of test shocks, fibrillation has not been induced, one or more additional rounds of test shocks are administered provided the system minimum level of shock strength, typically 5 J, has not been reached as determined in step 85. Each subsequent round utilizes a lower shock strength from that value used in the previous round at step 70 based on the shock decrement value. If fibrillation has not been induced even at the system minimum, 5 J level as determined in step 85, the ULV is calculated to be equivalent to 5 J in step 87, and the defibrillation shock strength is set to a level incrementally above the ULV.

In an alternative normal rhythm embodiment of the method, time delays are calculated in a similar fashion, except that they are based on measurements made in normal rhythm or atrial-paced rhythm. A time interval is calculated based on the interval between the detected QRS complex (as opposed to a pacer spike) and the peak of the time derivative of the selected intra-cardiac T-wave. In the alternative normal rhythm embodiment, step 76 also includes the sub-step of determining that the heart's rhythm is sufficiently regular that the time interval between the detected QRS complex and the peak of the derivative of the intra-cardiac T-wave is likely to be substantially constant over a few beats.

The principal advantage of the present invention is the capacity to automate determination of the optimal first shock strength for transvenous ICDs using only implanted electrodes by determining the ULV with improved accuracy, safety, speed and simplicity. The present invention is substantially improved over previous methods of determining the ULV for purposes of predicting the DFT and is of sufficient accuracy that conventional DFT testing is unnecessary. The time required for the procedure is substantially shortened by diminishing the number of episodes of fibrillation, the number of shocks in regular rhythm, the need to record a 12-lead surface ECG, and the need to make cumbersome measurements from the 12-lead surface ECG. The present invention is easy to apply because all measurements can be automated in the software of the ICD or programmer.

2. Methods for Improved Timing of T-wave Shocks

The timing systems, apparatus and method disclosed herein are useful with the devices and methods for determining defibrillation shock strength utilizing timed T-wave shocks in described above. In addition, they may be used with other devices and methods.

Digital signal processing techniques have been used in cardiac electrophysiology. For example, Köhler et al, used digital signal processing techniques for the purpose of improving the accuracy of automated detection of surface ECG signals.

The maximum of the first derivative of the T-wave is also an inflection point ($T_I$), corresponding to the zero point of the second derivative as the first derivative changes from concave up to concave down. Depending on the method used for calculation, this zero point of the second derivative may, under some conditions, be less susceptible to noise than the first derivative.

Analysis of two or more simultaneously acquired biological signals to measure an important parameter is well-established approach. Multiple methods and techniques have been developed to combine signals for this purpose.

In cardiac electrophysiology, previous investigators have combined either information from multiple electrograms or information from different methods of signal processing applied to the same electrogram. For example electrogram voltage, its first derivative with respect to time, and its second derivative with respect to time have been combined to improve discrimination of local signals from far-field signals in a single electrogram. Combinations of signals have been used to improve other solutions in electrocardiography, such as diagnosis of acute myocardial infarction.

The shape of cardiac electrical signals recorded from subcutaneous electrograms approximates, and is therefore similar to, that of the derivative of an intracardiac electrogram. Thus, in one embodiment of the invention, timing points from subcutaneous electrograms may be measured directly from the peak of the T-wave of the subcutaneous electrogram rather than from the derivative of its T-wave. Alternatively, since the derivative of the recovery phase of the action potential forms the T-wave of the subcutaneous electrogram, the integral of the T-wave of the subcutaneous electrogram is an accurate estimate of the action potential. For computational purposes, it may be preferable to integrate the subcutaneous electrogram and then differentiate the resulting integral to identify a fiducial point for T-wave shocks.

Concentric Laplacian electrodes have been used to increase signal quality of surface ECGs. One embodiment of the present invention uses subcutaneous Laplacian electrodes. The electrogram recorded from the Laplacian electrode is considered to be a second derivative of the intracardiac electrogram. Thus, the present invention integrates the signal from a subcutaneous Laplacian electrogram to obtain an approximation of $T_R$, which is measured from the first derivative of the intracardiac electrogram in the '042 patent.

The present invention utilizes plural signal processing techniques to time T-wave shocks. The electrogram recorded from the tip electrode 36 in the right ventricular to the distal coil 26 (Tip-Coil electrogram) often has an inflection point ($T_I$, zero of the second derivative) at a coupling interval close to that of the maximum of the first derivative of the far-field (Coil-Can) electrogram. At this inflection point, concavity changes from down to up as the second derivative changes from negative to positive. Preliminary data indicate that $T_1$ of the Tip-Coil electrogram usually occurs at a slightly shorter coupling interval than $T_R$ or $T_1$ of the Coil-Can electrogram. Combining timing point data from two electrograms such as the Tip-Coil and Coil-Can electrograms may improve the accuracy of timing points.

Figure 6:
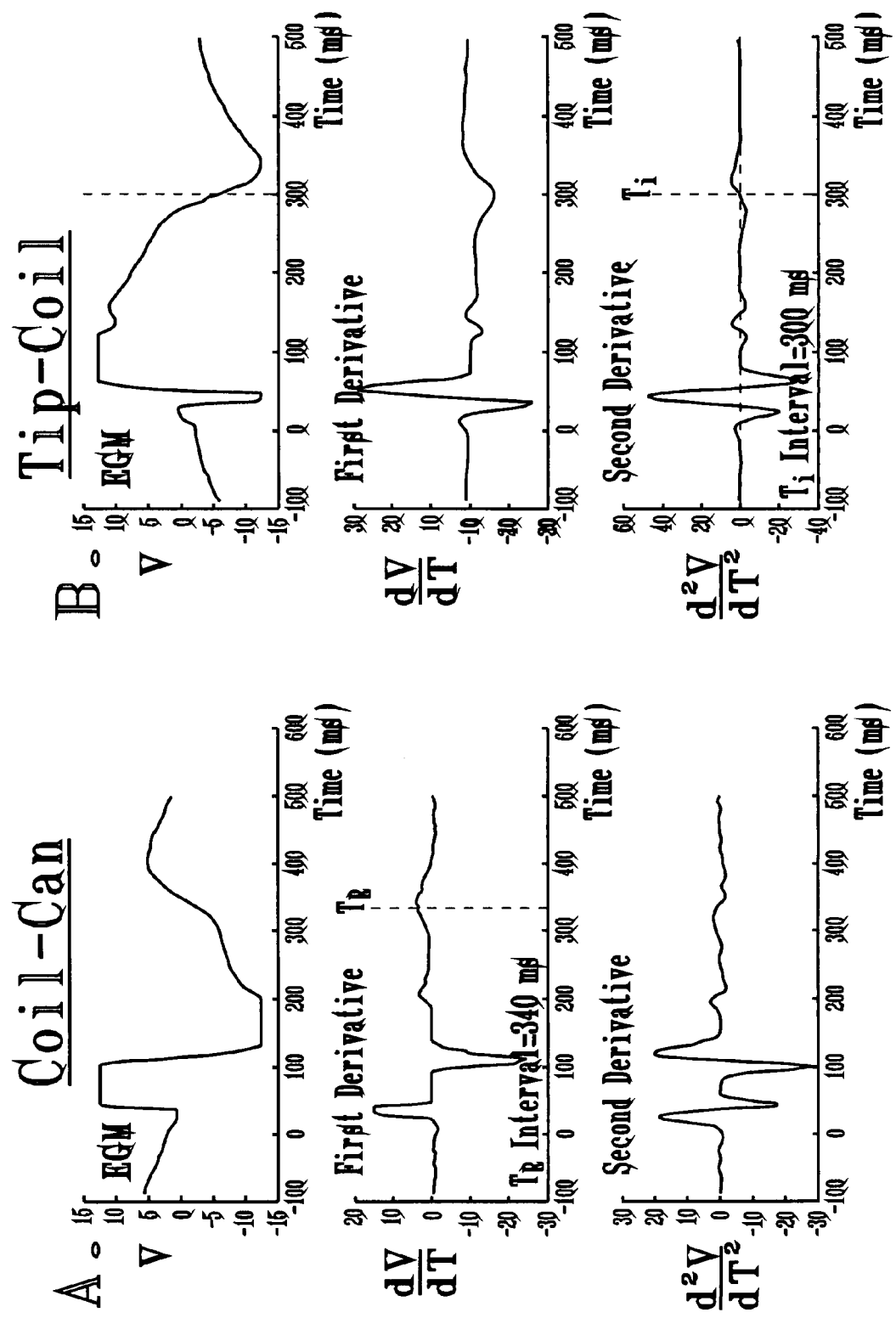
FIGS. 6A and B illustrate relative timing of electrograms and their derivatives.

FIG. 6 shows a representative example of relative timing of electrograms and their derivatives. Electrograms were recorded during right ventricular apical pacing at cycle length 500 ms. FIG. 6A shows a Coil-Can electrogram (labeled EGM) with its first and second derivatives. FIG. 6B shows the Tip-Coil electrogram (labeled EGM) with its first and second derivatives. In both FIG. 6A and FIG. 6B, the source electrogram is in top panel, the first derivative is in the middle panel, and the second derivative is in the bottom panel. In each panel, the abscissas shows time measured from the pacing stimulus. The ordinates are calibrated in mV for electrograms, mV/s for first derivatives, and $mV/s^2$ for second derivatives. In FIG. 6A middle panel, the vertical dotted line identifies the peak of the first derivative ($T_R$). In the FIG. 6B lower panel, the intersection of dotted vertical and horizontal lines identifies the zero point of the second derivative ($T_I$). $T_1$ in the lower panel of FIG. 6B corresponds to an inflection point on the Tip-Coil electrogram denoted by the dotted vertical line in the upper panel FIG. 6B. At this inflection point, concavity changes from down to up as the second derivative (lower panel) changes from negative to positive. $T_1$ in the Tip-Coil electrogram (FIG. 6B) precedes $T_R$ in the Coil-Can electrogram (FIG. 6A) by about 40 ms. These electrograms were recorded at 50 mms paper speed on the Medtronic 2090 programmer, scanned, and digitized using Data Thief®. Then they were differentiated and smoothed using Matlab®.

Figure 7:
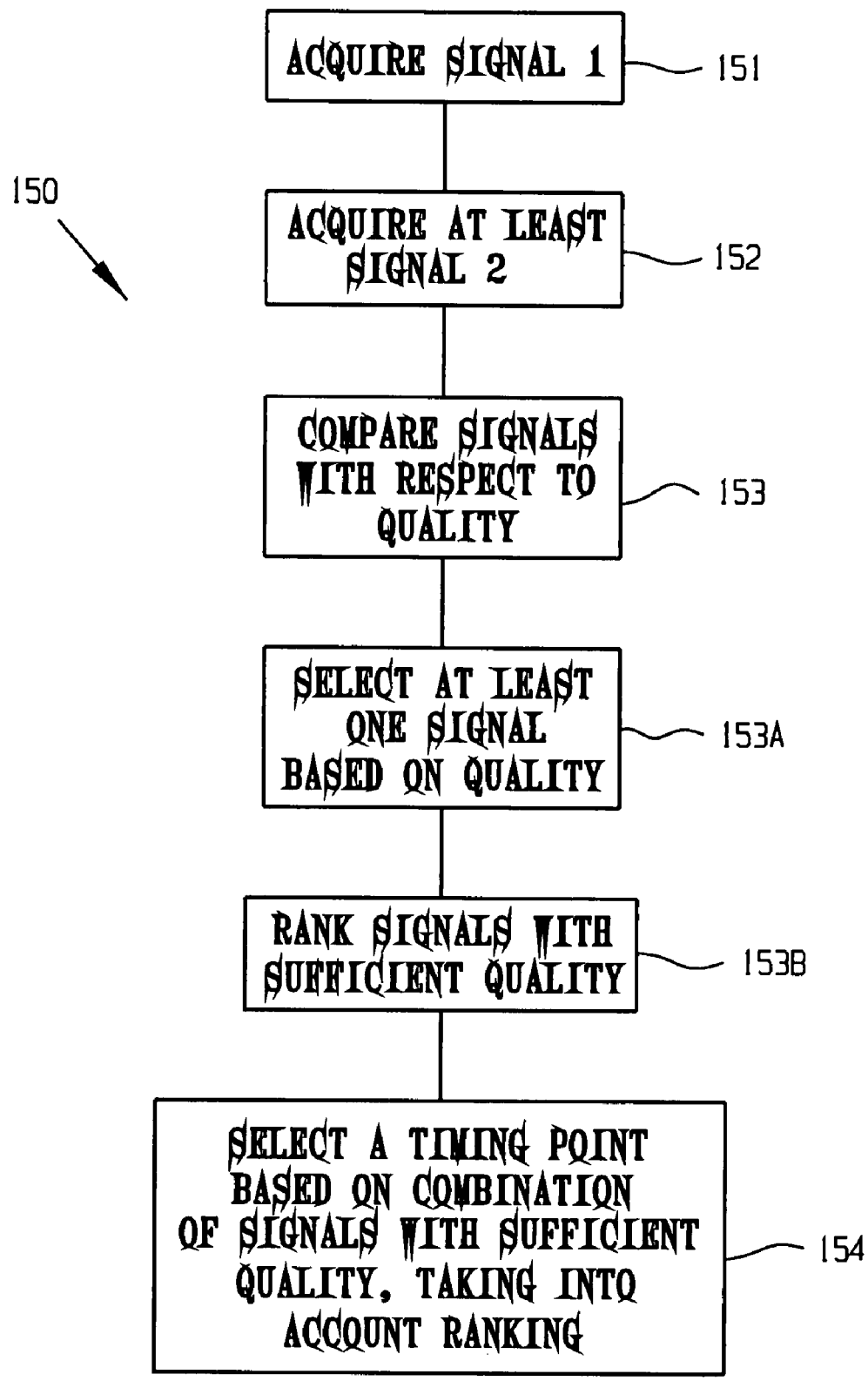
FIG. 7 is a flow chart of an embodiment of the basic method of selecting a T-wave timing point.

Referring to FIG. 7, a basic method 150 of the present invention, a first 151 and at least one second 152 signals are acquired and a comparison method 153 is applied to determine how to select 154 the timing point within the T wave. These signals are either electrograms or signals derived from electrograms, such as their derivatives or integrals. These signals may be derived from the same electrogram (e.g. different derivatives) from different electrograms, or some combination thereof. The quality of each signal quality is measured as described below.

An embodiment of the method of the present invention for selecting 154 the timing point is as follows:
  a. The electrogram signals are ranked according to quality.
  b. If more than one signal has sufficient quality, the priority in which signals are used to select the timing point within the T-wave is specified in advance by predetermined instructions. Offset times of shocks may be different, depending on the specific signal or combination of signals that is used to select timing points.
  c. Various methods may be used to select timing points including, but not limited to, the maximum value, minimum value, and minimum absolute value (zero point) on a time interval.
  d. If more than one signal has sufficient quality, the timing interval for the shock may be selected from a mathematical combination of the intervals from the predetermined fiducial base timing point (prior to the T-wave, usually the pacing stimulus or sensed R wave) to each of the timing points within the T-wave that can be determined with sufficient quality. Offset times (see (b) may be added to (or subtracted from) the value used for some timing points to normalize them. Possible methods for mathematical combinations are described below.

Figure 8A:
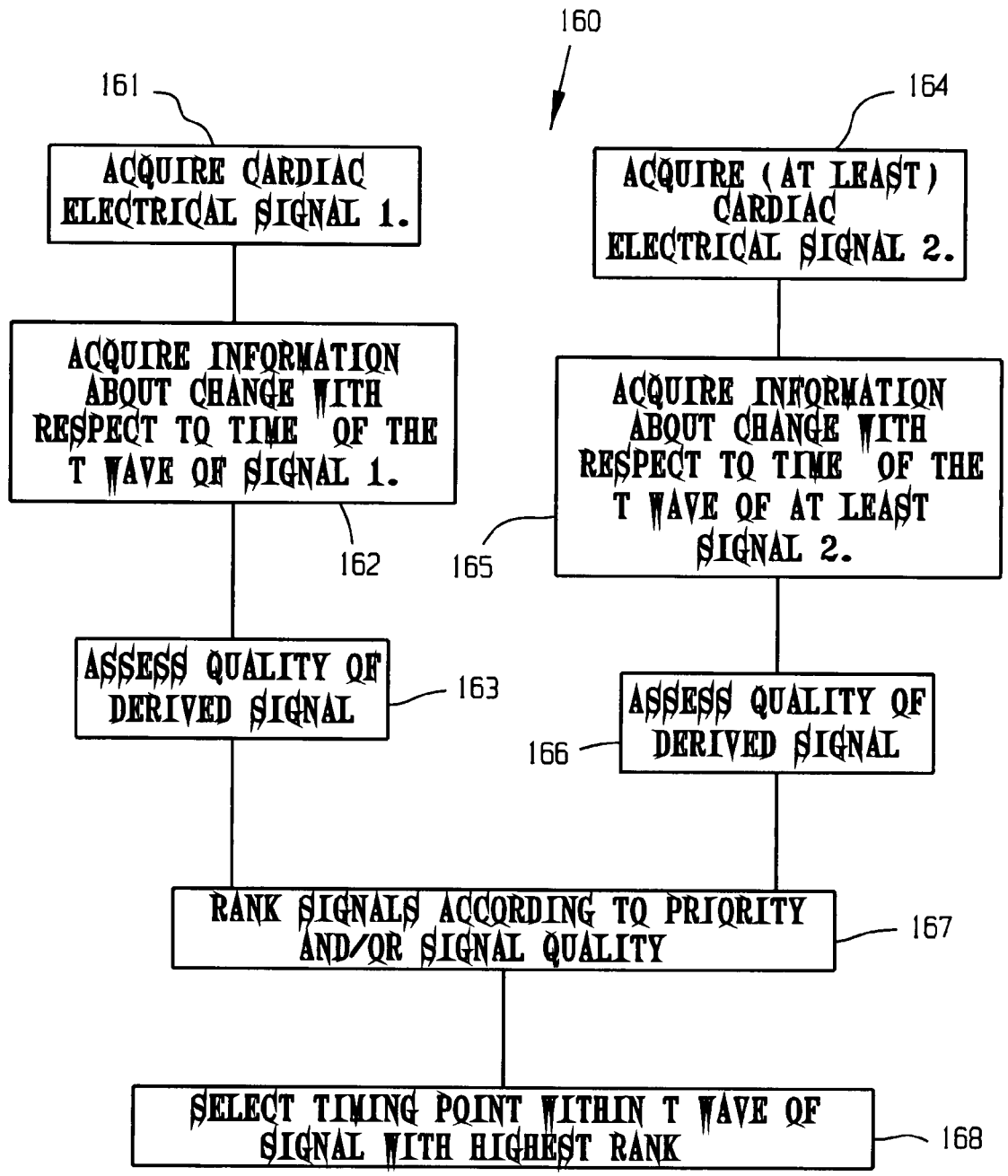
FIG. 8A is a flow chart of an alternative, particular embodiment of the method of selecting a T-wave timing point based on one type of change with respect to time in at least two different electrical cardiac signals.

The method of selecting timing points may be applied with respect to multiple signals in various ways. Referring to FIG. 8A, one such way 160 comprises the steps of acquiring a first cardiac electrical signal 161, acquiring information about a change with respect to time of the T-wave in said first electrical cardiac signal 162, and assessing the signal quality of the derived signal representing the change with respect to time of the first signal 163. Simultaneously or sequentially, the method 160 also comprises the steps of acquiring at least a second, different cardiac electrical signal 164, acquiring information about the same change with respect to time of the T-wave(s) in said at least a second electrical cardiac signal(s) 165, and assessing the signal quality of the derived signal(s) representing the change with respect to time of the at least second signal 166. The base method further comprises the step of comparing the first and at least one second derived electrical cardiac signal information 163, and thus ranking these derived signals in relation to priority and/or signal quality 167. The base method finally includes selecting timing points within the T-wave 164 based on the comparison step 168.

Figure 8B:
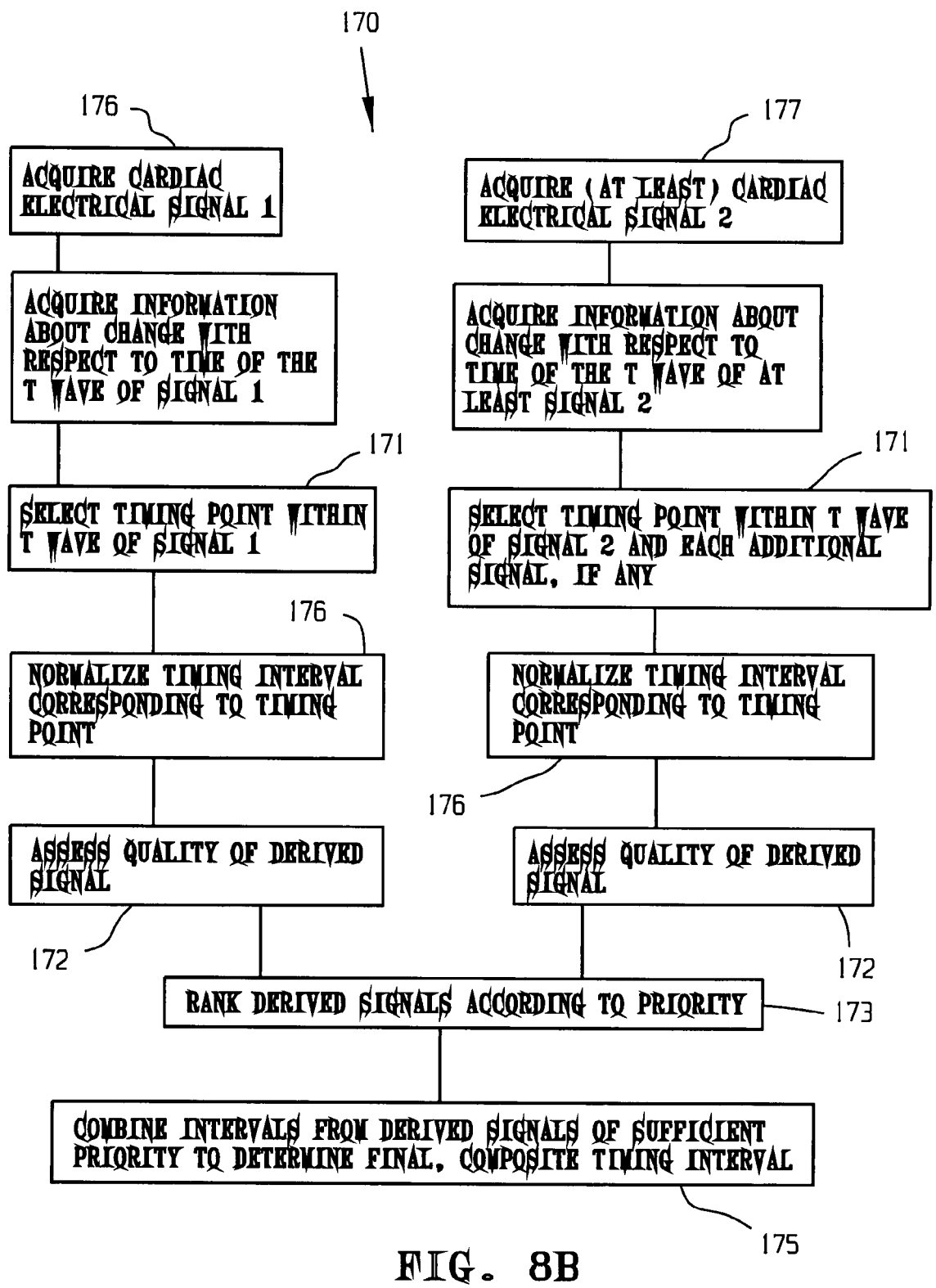
FIG. 8B is a flow chart of a more particular embodiment of the method of selecting a T-wave timing point of FIG. 8A, wherein the two different electrical cardiac signals are the Tip-Coil electrogram and the Coil-Can electrogram.

A more particular way 170 of implementing the process of FIG. 8A is shown in FIG. 8B. The process 170 comprises the steps of selecting 171 a timing point within the T wave of the first derived signal, the second and each additional derived signal, optionally assessing the quality of each derived signal 172, and ranking the derived signals according to quality 173. The intervals corresponding to these timing points may optionally be normalized 174 depending on the source electrogram by adding or subtracting a fixed interval or percent of the interval in the range of 20-60 ms. Alternatively steps 172 can be performed simultaneously with or before steps 171. Base method 170 finally comprises the step 175 of combining intervals from derived signals of sufficient priority to determine a final composite interval used for timing the T wave shock.

Referring again to FIG. 8A, a particular way of implementing the basic method 160 (and/or process variant 170) is to use a first electrogram from a Coil-Can 161, and the second electrogram from a Tip-Coil 164. These different electrograms are compared 162, 166 and selected 167. $T_1$ may be normalized by adding a value in the range of 20-60 ms before applying the mathematical combination.

Figure 8C:
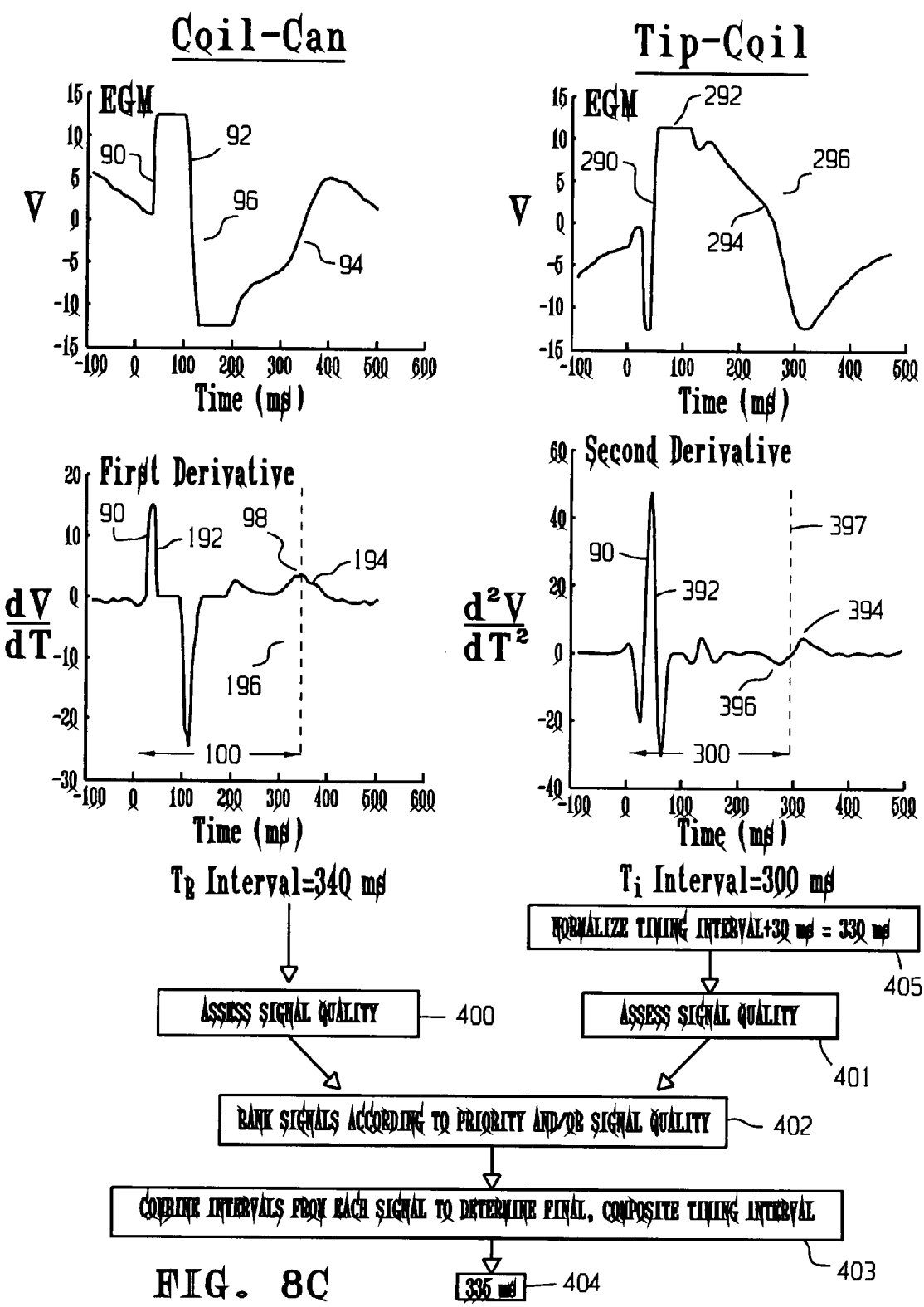
FIG. 8C is a flow chart showing a mode detailed representation of the embodiment depicted in FIG. 8B.

FIG. 8C provides yet a more detailed example of FIG. 8B using the actual data from FIG. 6. The left upper panel (corresponding to FIG. 6A top panel) shows the intra-cardiac Coil-Can electrogram 96 (labeled EGM), the pacer spike 90, QRS complex 92, and the T-wave 94. The left lower panel (corresponding to FIG. 6A middle panel) shows the first derivative of the Coil-Can electrogram 196 including the first derivative of the QRS complex 192, and the T-wave 194. The base time interval 100 is measured between the pacer spike 90 and the maximum (peak) 98 of the first derivative of the T-wave 194. This timing interval determines $T_R$ is approximately 340 ms. The signal quality of the first derivative of the Coil-Can electrogram is assessed in step 400, which may be performed prior to or contemporaneously with determination of base timing interval 100.

The upper right (corresponding to FIG. 6B top panel) panel shows the right-ventricular Tip-Coil electrogram 296, the pacer spike 290, QRS complex 292, and the T-wave 294. The lower right panel (corresponding to FIG. 6B bottom panel) shows the second derivative of the Tip-Coil electrogram 396 including the first derivative of the QRS complex 392, and the T-wave 394. The base time interval 300 is measured between the pacer spike 90 and the zero point 397 of the second derivative of the T-wave 394. This timing interval determines $T_i$ is approximately 300 ms. The signal quality of the second derivative of the Tip-Coil electrogram is assessed in step 401, which may be performed prior to or contemporaneously with determination of base timing interval 300. In this example, the interval corresponding to the inflection point of the Tip-Coil signal ($T_i$) is normalized by adding 30 ms. Further, in this illustration, signal quality is judged sufficient for both signals. The signals are then ranked according to priority in step 402.

In this illustration, the two signals receive equal priority. In step 403, the individual intervals from each signal are combined to determine a final, composite timing interval. In this illustration, the method used for comparison is a simple average of the individual interval determined from the individual signals. The resultant composite timing interval is 335 ms.

Figure 9A:
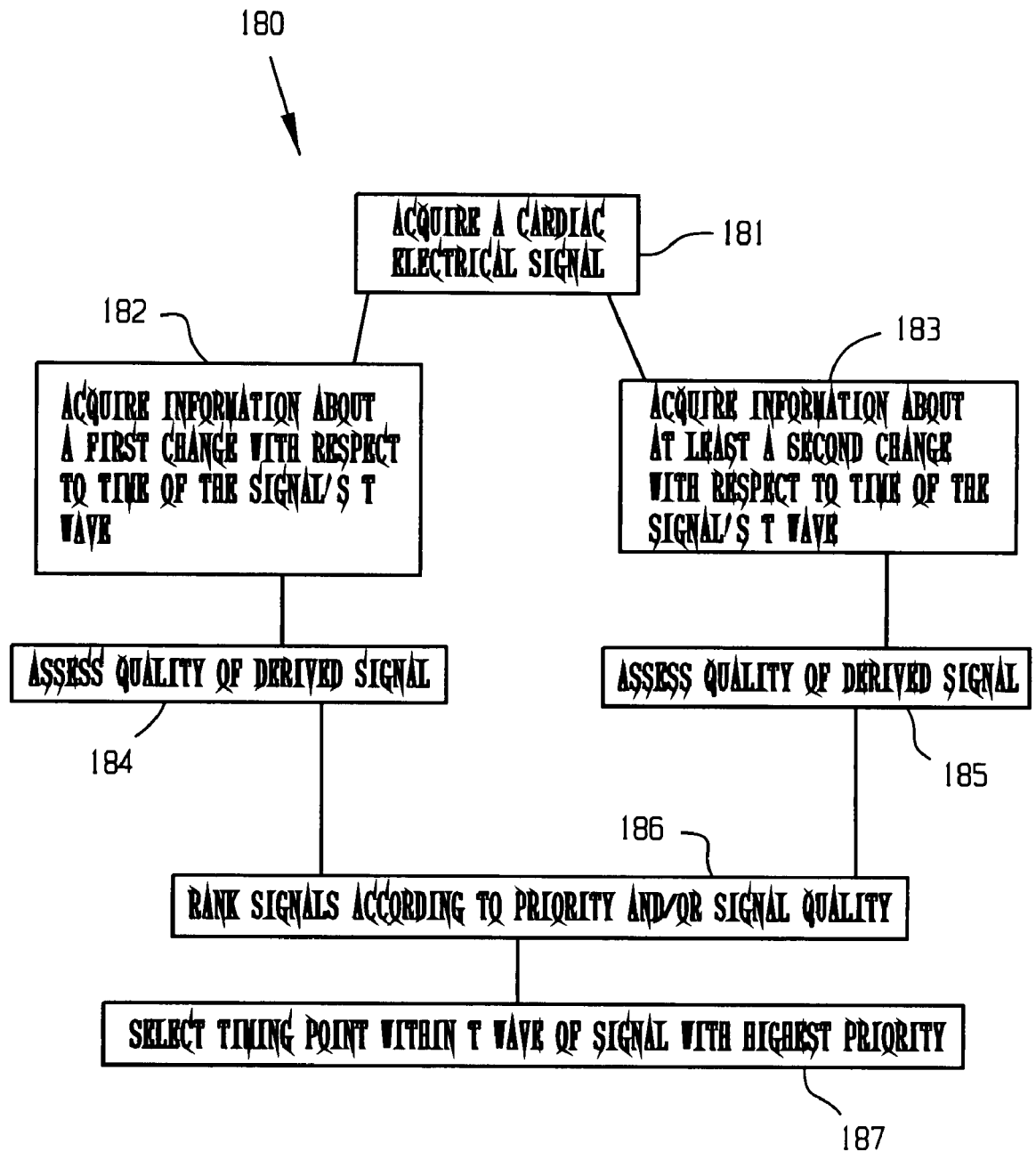
FIG. 9A is flow chart of a particular embodiment of a method of selecting a T-wave timing point based on at least two different changes with respect to time in the same electrical cardiac signal.

Referring to FIG. 9A, an alternative way of selecting timing points within the T wave, with respect to multiple signals, involves using a single electrogram and calculating two different changes with respect to time of that single electrogram 181. The basic method 180 comprises the steps of acquiring information about a first change with respect to time in a T-wave of an electrical cardiac signal 182, acquiring information about at least one second, and different change with respect to time in a T-wave of the same electrical cardiac signal 183, assessing the signal quality of each derived signal representing a change with respect to time in steps 184 and 185, ranking the signals according to priority and/or signal quality in step 186, and then selecting a timing point within the T wave of the signal with the highest priority in step 187.

Figure 9B:
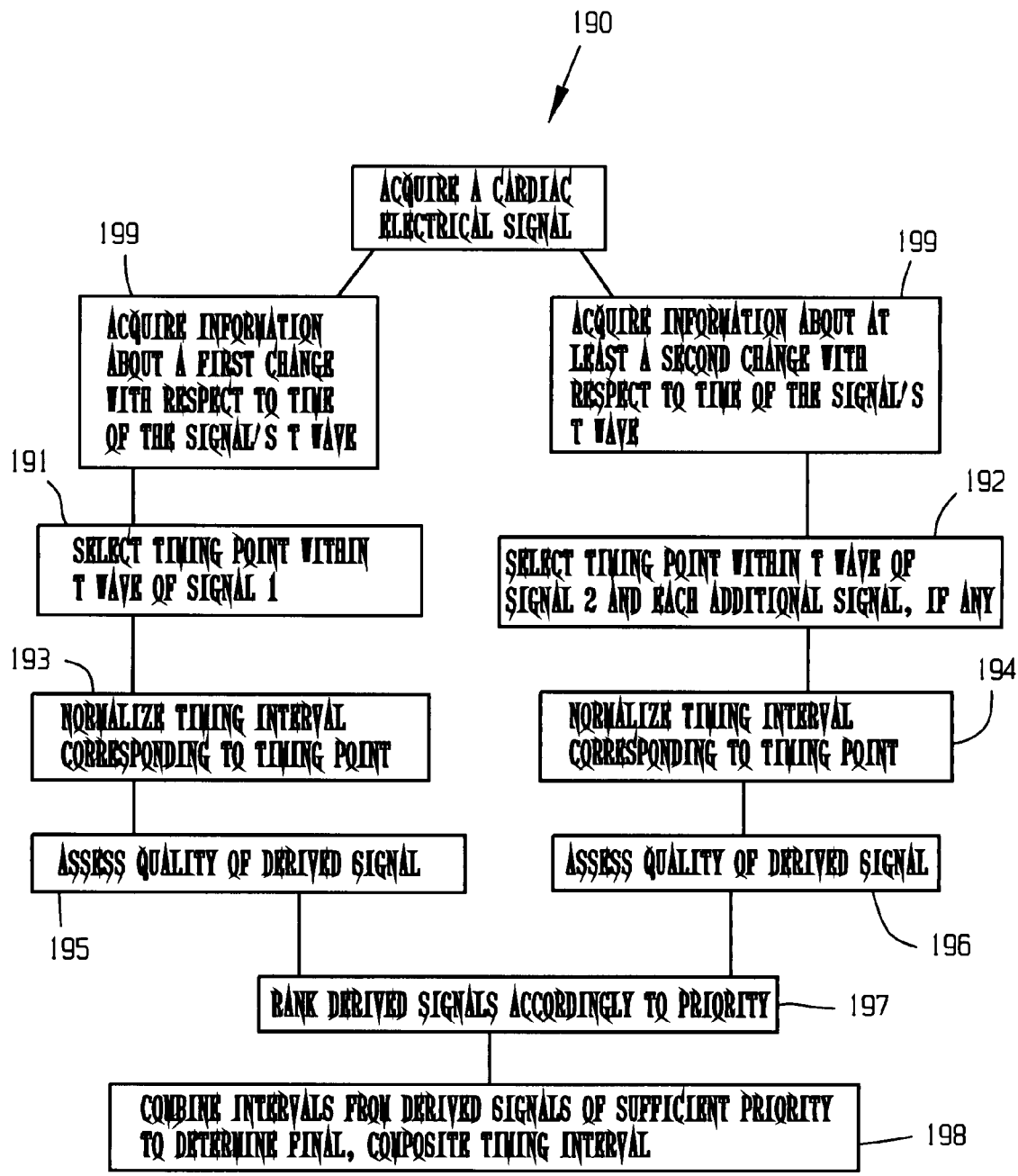
FIG. 9B is a flow chart of a more particular embodiment of the method of selecting a T-wave timing point of FIG. 9A, wherein the two different changes with respect to time are the maximum of the first derivative of the T-wave and the zero point of the second derivative of the T-wave.

FIG. 9B shows an alternative, and more particular process 190 than the embodiment shown in FIG. 9A. After the timing points are selected in steps 191 and 192, the corresponding timing intervals may optionally be normalized in steps 193 and 194 by adding or subtracting a fixed value or percent. The quality of each derived signal representing a change with respect to time is assessed in steps 195 and 196, and then the signals are ranked according to priority based on signal quality and the specific nature of each derived signal in step 197. Finally, intervals from derived signals of sufficient priority are combined to determine final, composite interval used for timing T-wave shocks in step 198.

In a particular example 190 of this method variant, shown in FIG. 9A, the first change with respect to time may be the first derivative 182 and the second change with respect to time may be the second derivative 183. Then signal quality would be evaluated 184/185 first for $T_R$ and $T_i$ of the single electrogram (for example Coil-Can). The invention will select 187 the timing point as the signal with the better quality.

Figure 9C:
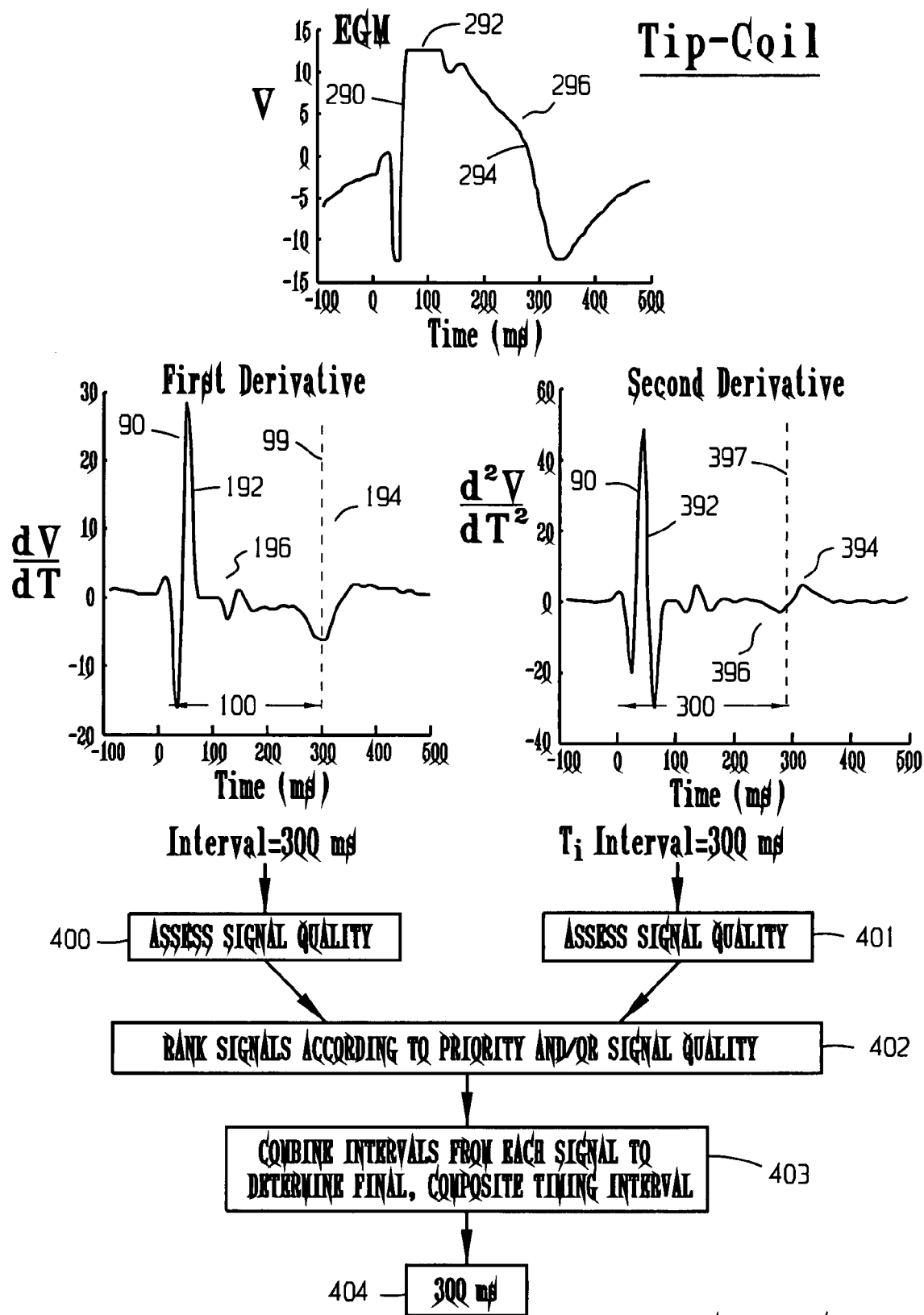
FIG. 9C is a flow chart showing a mode detailed representation of the embodiment depicted in FIG. 9B.

FIG. 9C provides yet a more detailed example of FIG. 9B using the actual data from FIG. 6. The upper panel (corresponding to FIG. 6B top panel) show the right-ventricular Tip-Coil electrogram 296, the pacer spike 290, QRS complex 292, and the T-wave 294. The left lower panel (corresponding to FIG. 6B middle panel) shows the first derivative of the Tip-Coil electrogram ("First Derivative") 196 including the first derivative of the QRS complex 192, and the T-wave 194. The base time interval 100 is measured between the pacer spike 90 and the maximum absolute value 99 of the first derivative of the T-wave 394. Note that this maximum absolute value is actually a minimum value of the derivative. Thus this timing interval of approximately 300 ms does not correspond to the recovery time ($T_R$). The signal quality of the first derivative is assessed in step 400, which may be performed prior to, contemporaneously with, or after determination of base timing interval 100.

The lower right panel (corresponding to FIG. 6B bottom panel) shows the second derivative of the Tip-Coil electrogram ("Second Derivative") 396 including the first derivative of the QRS complex 392, and the T-wave 394. The base time interval 300 is measured between the pacer spike 90 and the zero point 397 of the second derivative of the T-wave 394. This timing interval determines $T_i$ is approximately 300 ms. The signal quality of the second derivative is assessed in step 401, which may be performed prior or contemporaneously with or after determination of base timing interval 300.

The signals are then ranked according to priority and/or signal quality in step 402. In this illustration, signal quality is judged sufficient for both signals. Hence, the two derivative signals receive equal priority. In step 403, the individual intervals from each derivative signal are combined to determine a final, composite timing interval. In this illustration, each derivative gives the same timing interval of 300 ms. The method used for comparison is a simple average of the individual interval determined from the individual signals. The resultant composite timing interval is 300 ms.

Figure 10:
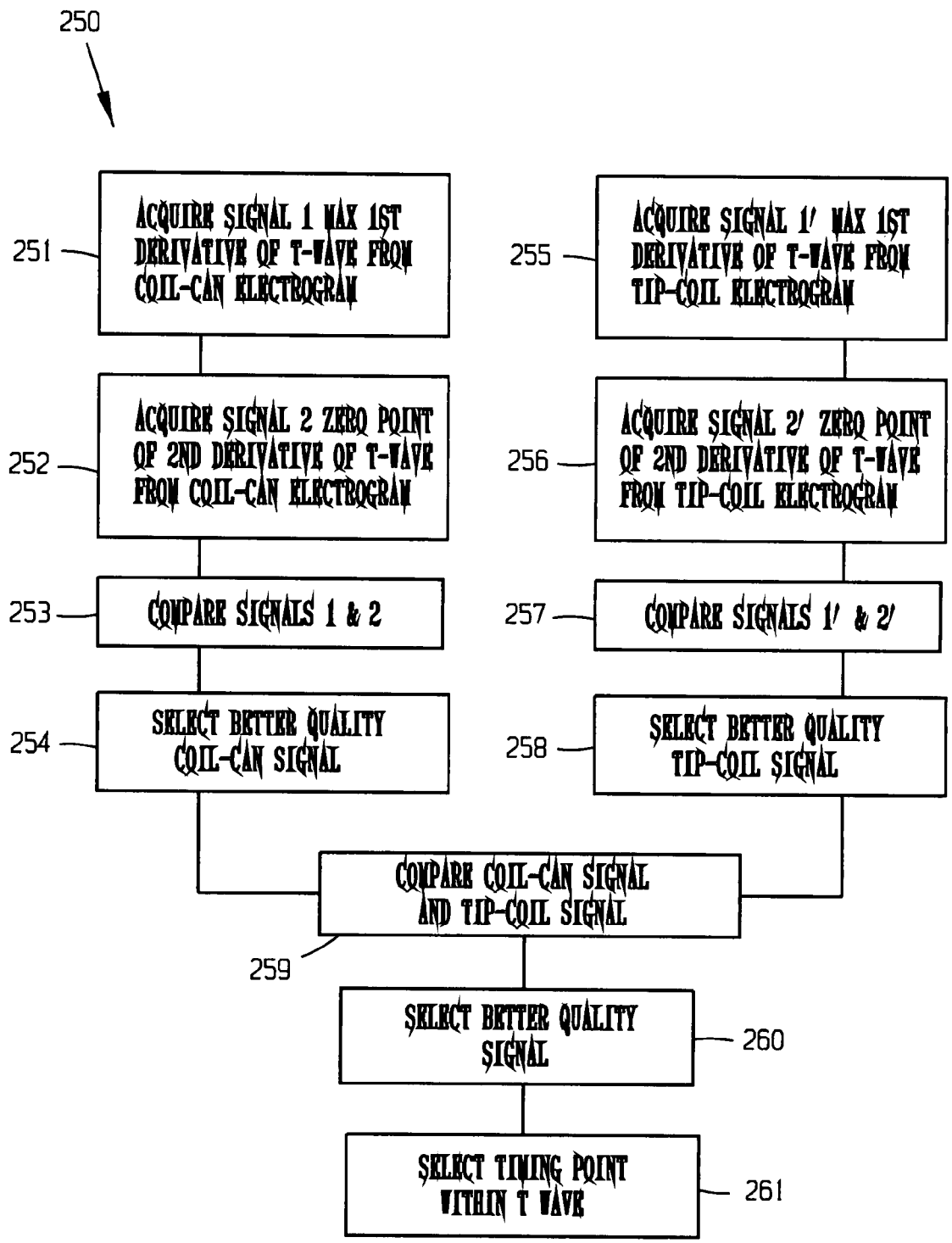
FIG. 10 is a flow chart of yet another alternative, particular embodiment of selecting a T-wave.

Referring to FIG. 10, in a third embodiment, signal quality would be evaluated first for $T_R$ (computed from the first derivative) and $T_i$ (computed from the second derivative) of a single electrogram (e.g. Coil-Can). The invention will combine the derived signal with the better quality from the first electrogram with a signal from a second electrogram such as $T_I$ of the Tip-Coil electrogram. Particularly, an embodiment of this method 250 involves the step of acquiring signal 1, the maximum of the first derivative of the T-wave from the coil-can electrode 251, acquiring signal 2, the zero point of the second derivative of the T-wave of the coil-can electrogram, 152, then comparing signals 1 and 2, and then selecting the better quality signal from this electrogram 254. Simultaneously or subsequently, signal 1' is acquired, the maximum of the first derivative of the T-wave from the tip-coil electrogram 255, signal 2', and the zero point of the second derivative of the T-wave from the tip-coil electrogram is acquired 252. Signals 1' and 2' are compared 257 and the better quality signal is selected 258. Subsequent to the selections 254 and 258, the coil-can selected signal and the tip-coil selected signal are compared 259. The better quality of these two signals is selected 260. Based on this selection 260, one or more timing points are selected for the T-wave 261.

Figure 11:
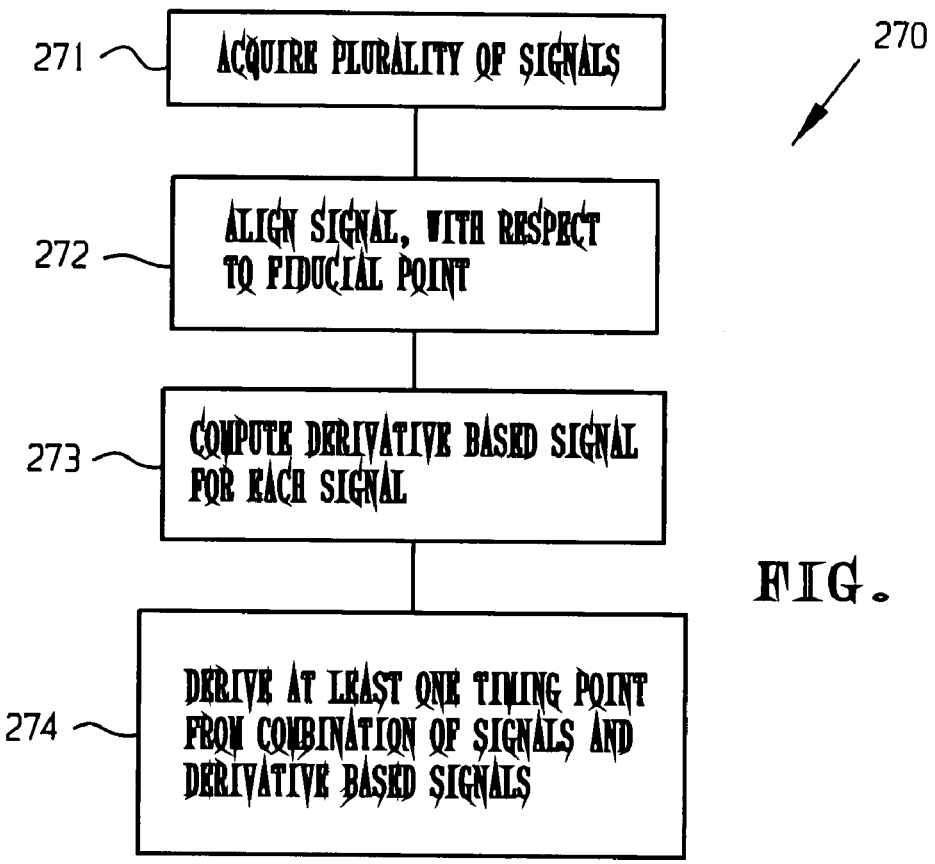
FIG. 11 is a flow chart illustrating an embodiment of a method of aligning signals for comparison purposes.

Referring to FIG. 11, the method 270 of determining a timing point from two or more simultaneously-acquired signals 271 involves aligning the recorded signals with respect to a pre-determined base timing point (fiducial point) 272. The fiducial point can be any pre-determined point in the cardiac cycle that can be detected from any electrogram recorded from an implanted electrode, surface ECG electrode, or an external clock. Examples of fiducial points from intracardiac electrograms include, but are limited to (1) the initial up-slope of the QRS complex, (2) the initial down-slope of the QRS complex, (3) the absolute maximum value of the QRS complex, (4) the J-point of the ST-segment, (5) first zero of the first derivative of the QRS complex, (6) the first zero of the first derivative of the QRS complex that occurs after the absolute value of the QRS complex reaches a predetermined minimum value, and (7) a pacing stimulus.

Using the fiducially-aligned set of electrograms, the invention computes a type of derivative signal for each electrogram (e.g. first derivative, second derivative, partial derivative, gradient, and other derivative-based signals) 273, and then the invention's method derives one or more important timing points from a combination of these derivatives and the original signals 274. Depending on pre-determined parameters input to the invention, the invention can also use the same electrogram to compute two or more different types of derivative signals. These two or more signals derived from a single electrogram can be used to compute one or more timing points.

Figure 12:
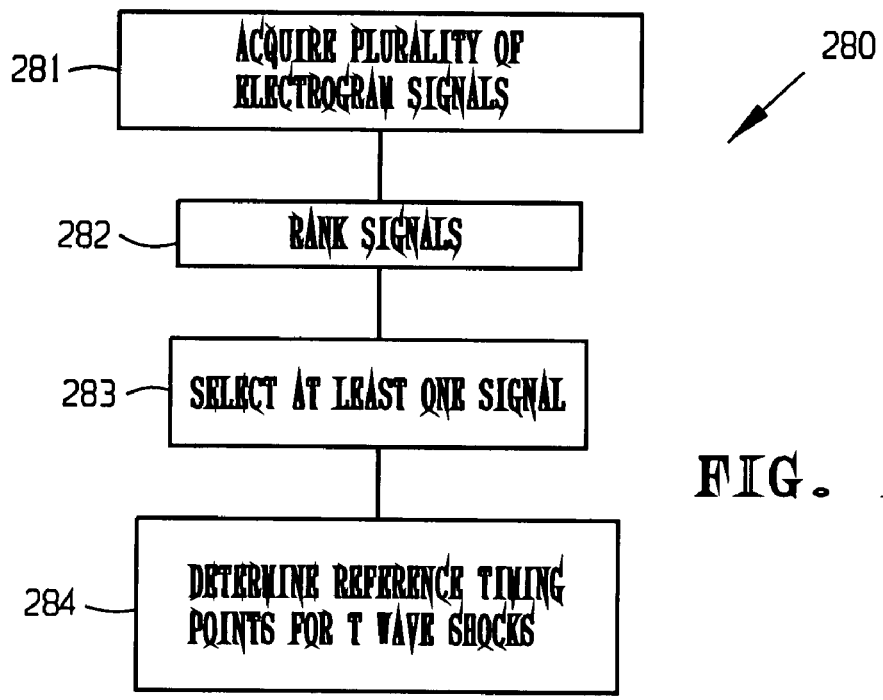
FIG. 12 is a flow chart illustrating an embodiment of a method of qualitative analysis of signals.
Figure 13:
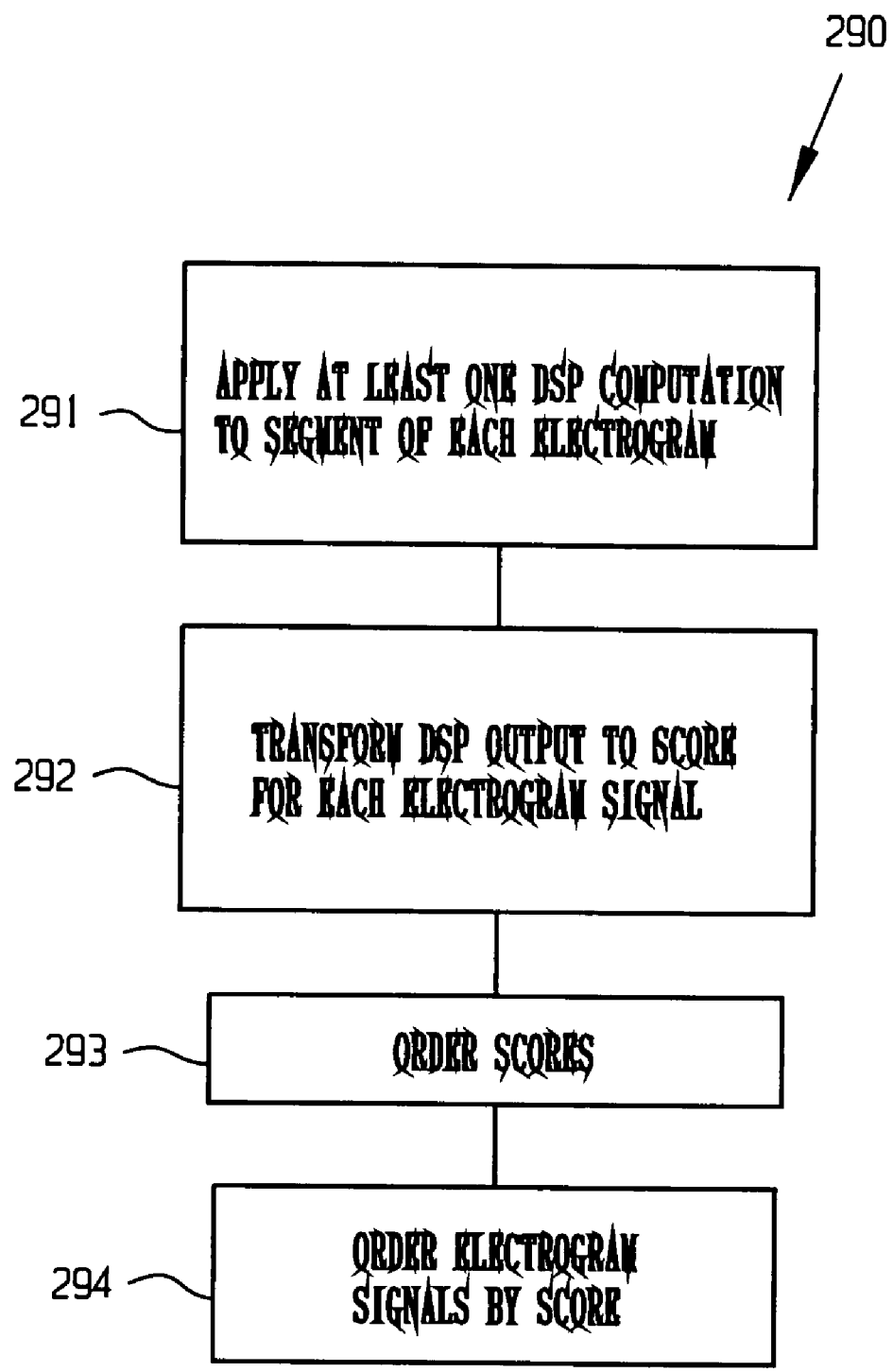
FIG. 13 is a flow chart illustrating an embodiment of a method of ranking signals used in the method of FIG. 12.
Figure 14:
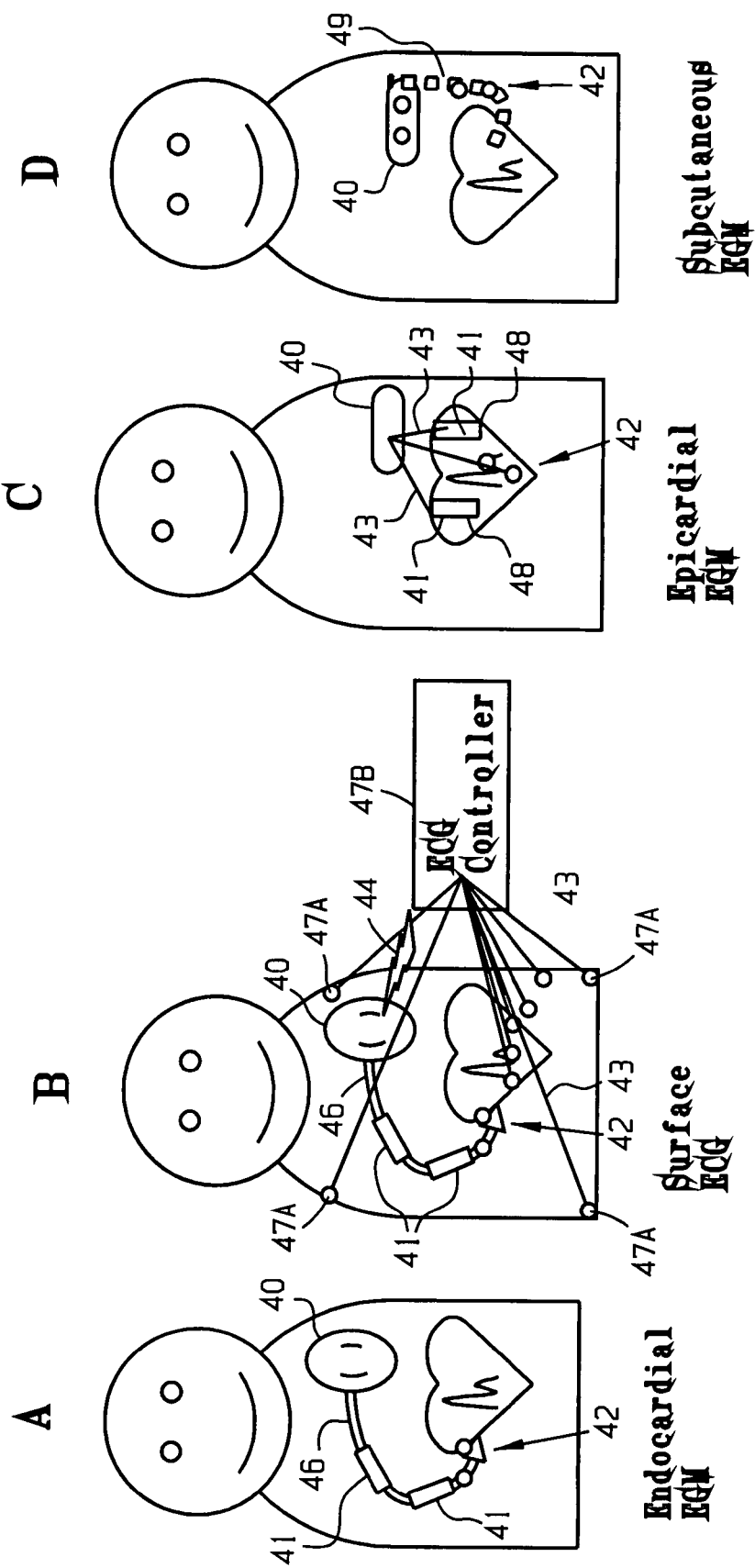
FIGS. 14 and 15 show exemplary electrode placements consistent with the invention.
Figure 15:
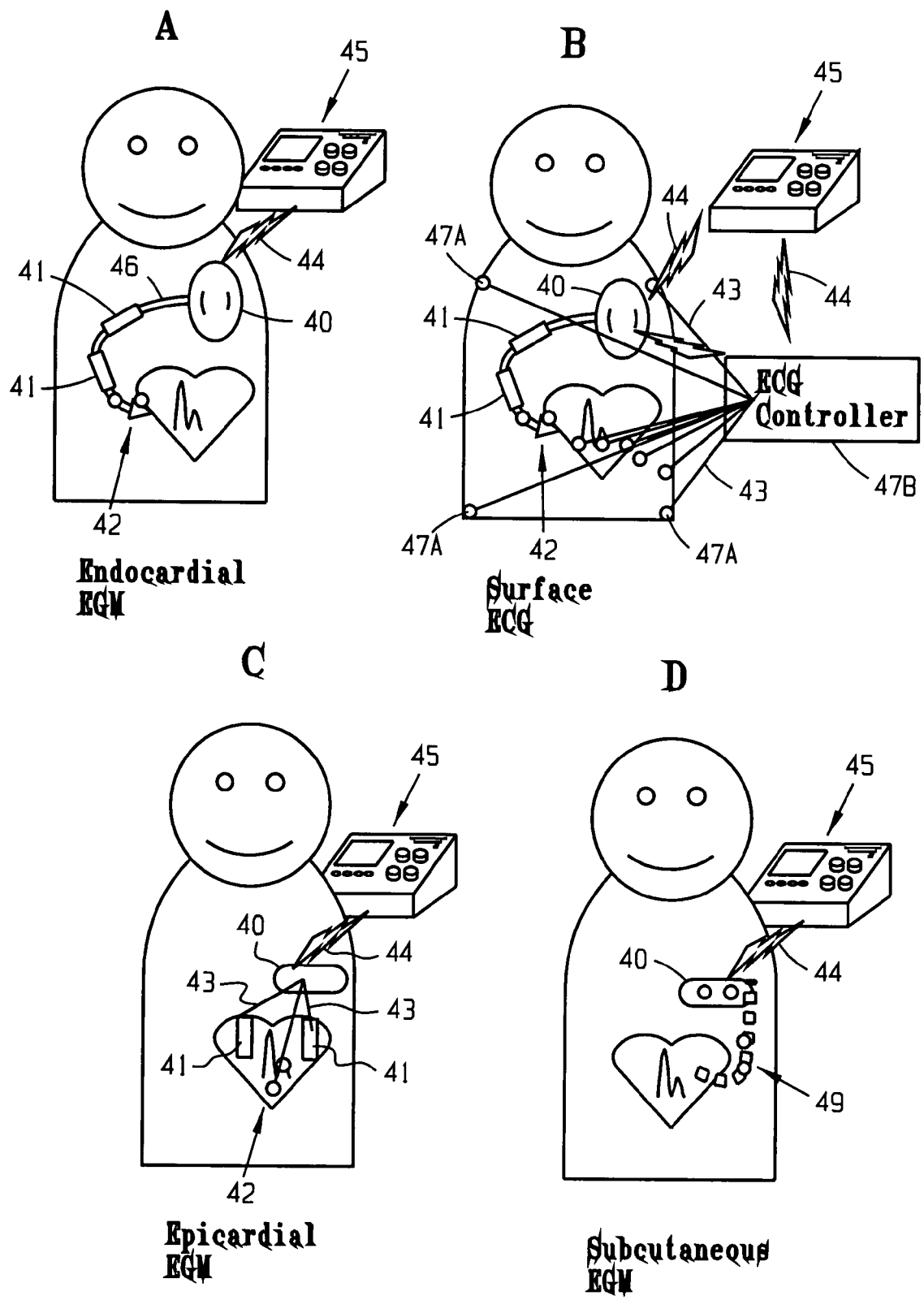

An illustrative subset of multiple signal-based computations that can be applied to the set of fiducially aligned electrograms (or electrogram segments) and their derived signals (such as derivatives and integrals), wherein a signal value is also called a parameter value, include:

(a) computing one or more timing points for each original or derived signal, which may include all points in time in the T wave, and computing a weighted (arithmetic, geometric, harmonic) average using the parameter values relating to the timing points;

(b) computing one or more timing points for each original or derived signal, which may include all points in time in the T wave, and computing a weighted ratio or weighted log-ratio using the parameter values relating to the timing points;

(c) computing one or more timing points for each original or derived signal, which may include all points in time in the T wave, and selecting a single parameter value relating to these timing points based on methods to analyze the set of timing points to select the single parameter value;

(d) selecting a single parameter value from the set of timing points computed in (a), (b) and (c). As illustrative examples, the single parameter value may be selected by the method used for computing it or by sorting the set of timing-point values and selecting the minimum, mean, medium, or maximum of such values;

Referring to FIGS. 12 and 13, electrogram signal quality can be evaluated by applying one or more well-known digital signal processing (DSP) techniques to the electrograms used by this invention. As is shown in FIG. 12, one method 280 first involves acquiring at least two electrogram signals 281. The level of signal quality determined by DSP techniques is used to rank the set of electrogram signals from lowest to highest quality 282. The invention selects a pre-determined number of the higher quality electrograms 283 that will be used to determine reference timing point(s) for T-wave shocks 284.

Referring to FIG. 13, first, the method 290 applies one or more of DSP-based computations to a pre-determined signal segment (such as a T wave segment) derived from each electrogram 291. The pre-determined period can range from the smallest measured interval to the entire duration of the electrogram signal. Typically, the period comprises between 25 and 250 ms, corresponding to the duration of a single T wave. Then the invention transforms 292 the output from the signal-based computations into a quality ranking score from lowest quality to highest quality 293. Lastly, the invention ranks each electrogram by its signal quality using a quality ranking score 294.

An illustrative subset of DSP-based computations that can be applied to each electrogram or electrogram segment are:

(a) computing standard time-domain measures of signal quality, such as the minimum, mean, median, or maximum signal value over a pre-determined period of time;

(b) computing the average signal difference from its mean (signal difference), by summing the absolute value of the differences of all the individual samples from the signal mean and dividing by the number of samples;

(c) computing the power of the average signal deviation from its mean (signal variance), by summing the square of the absolute value of the deviations of all the individual samples from the signal mean and dividing by the number of samples;

(d) computing the square root of the signal power (signal deviation);

(e) computing the signal to noise ratio (SNR), by dividing the signal mean by the signal deviation, and where higher signal quality is indicated by a larger SNR value;

(f) computing the coefficient of signal variation (CSV), by dividing the signal deviation by the signal mean (or taking the reciprocal of the SNR), and where higher signal quality is indicated by a smaller CSV value;

(g) computing the standard signal error, by dividing the signal deviation by the square root of the number of samples;
(h) computing one or more of the standard signal quality estimates (a) through (g) for a first segment of a signal, computing one or more of the standard signal quality estimates (a) through (g) for a second segment of the same signal, and computing signal quality ratios using the first and second signal segment quality estimates;
(i) constructing the signal histogram, based on signal values, and deriving various signal quality measures from the histogram, such as the signal mean and signal deviation;
(j) constructing a first histogram based on a first segment of a signal, deriving signal quality estimates from the first histogram, constructing a second histogram based on a second signal segment, deriving signal quality estimates from the second histogram, and computing signal quality ratios using the first and second signal segment quality estimates;
(k) computing the frequency content of a signal or signal segment, and using the frequency (spectral) content to then compute standard frequency-domain measures of signal quality analogous to the previously described time-domain measures, such as the minimum, mean, median, or maximum frequency value;
(l) computing the frequency content of a signal or signal segment, and then computing the signal segment phase shift, and determine signal quality by the minimum, mean, median, or maximum phase shift value;
(m) computing the frequency spectrum of a signal or signal segment and determining signal quality by the number, the minimum, mean, median, or maximum harmonic;
(n) computing the power spectrum of a signal or signal segment and determining signal quality by the amount of signal power in a pre-determined frequency range;
(o) applying a pre-defined test signal to a signal segment using time-domain-based convolution or correlation techniques, and using the output from a convolution or correlation technique computes a measure of signal quality, by ranking how well the signal segment matches the test signal;
(p) computing the frequency content of a signal segment, then applying a pre-defined test signal to a signal segment using frequency-domain-based multiplication or modulation techniques, and using the output from a multiplication or modulation technique computes a measure of signal quality, by ranking how well the signal segment matches the test signal;
(q) first applying a finite impulse response (FIR) filter to a signal or a signal segment, thereby accentuating pre-determined time-domain and frequency-domain signal content and parameters, and then applying any combination of one or more of the techniques (a) through (p); and
(r) first applying an infinite impulse response (IIR) filter to a signal or a signal segment, thereby accentuating pre-determined time-domain and frequency-domain signal content and parameters, and then applying any combination of one or more of the techniques (a) through (p).

Other DSP-based signal parameters can also be computed to measure signal quality.

Although the embodiments of the invention are for an ICD used for human medical purposes, the multiple signal processing methods, qualitative signal measurement method and signal alignment methods may be used in other devices and fields.

The descriptions above and the accompanying drawings should be interpreted in the illustrative and not the limited sense. While the invention has been disclosed in connection with an embodiment or embodiments thereof, it should be understood that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for accurately timing T-wave shocks, comprising the steps of: (a) deriving a first signal from a cardiac electrical signal from a system for determining implantable cardioverter defibrillator cardiac shock strength, wherein the first derived signal relates to a change with respect to time of the T wave of the cardiac electrical signal (b) deriving at least a second signal from a cardiac electrical signal from the system, wherein the at least second derived signal relates to a change with respect to time of the T wave of its respective cardiac electrical signal, (c) comparing the first derived signal and the at least one second derived signal, and (d) based on the comparison, selecting one or more timing points within the T wave of at least one of the derived signals for delivering shocks.

2. method of claim 1 wherein the comparing step includes quantitative analysis.

3. The method of claim 1 in which a timing point is selected within a T wave of each of the at least two derived signals and further comprising the step of applying an analytical step to determine a final, composite timing point based on the individual timing points selected from the at least two derived signals.

4. The method of claim 1, wherein the first and at least one second derived signals are different changes with respect to time from a single cardiac electrical signal.

5. The method of claim 1, wherein the first and at least one second derived signals are the same change with respect to time of a first cardiac electrical signal and at least one second, different, cardiac electrical signal.

6. The method of claim 1, wherein the first and at least one second derived signals are different changes with respect to time of a first cardiac electrical signal and at least one second, different, cardiac electrical signal.

7. The method of claim 1, wherein comparison includes signal alignment.

8. The method of claim 1 further comprising the step of computing the one or more timing points utilizing one, some, or all points in time in the T wave of the derived signal.

9. The method according to claim 8, wherein the one or more timing points are computed via an arithmetically, geometrically, or harmonically weighted average using parameter values relating to the timing points.

10. The method according to claim 8 wherein the one or more timing points are computed via a weighted ratio or weighted log-ratio using parameter values relating to the timing points.

11. The method of claim 8 in which a single parameter value is selected relating to a set of one or more timing points based on methods to analyze the set of timing points.

12. The method according to claim 11, wherein the single parameter value is selected by sorting the one or more timing point values and then selecting one of the timing points.

13. The method according to claim 12, wherein the single parameter value relates to the minimum, mean, median, mode, or maximum of the values of the timing points.

14. The method of claim 1, wherein at least one timing point is an extreme absolute value of the change with respect to time, selected from the group consisting of a minimum absolute value, a minimum value, and a maximum value.

15. The method of claim 1, further comprising the step of calculating at least one said change with respect to time by a finite difference, an ordinary derivative, a directional derivative, a gradient and a partial derivative, an implicit differential, a variance calculation, a bounded variation calculation, a radial displacement vector, or a tangent vector approximation.

16. The method of claim 14, further comprising the step of calculating the extreme absolute value by a method selected from the group of calculation methods consisting of a finite difference, an ordinary derivative, a directional derivative, a gradient and a partial derivative, an implicit differential, a variance calculation, a bounded variation calculation, a radial displacement vector, and a tangent vector approximation.

17. The method of claim 1, wherein a change with respect to time is the first derivative of T wave amplitude with respect to time.

18. The method of claim 1, wherein a change with respect to time is the second derivative of T wave amplitude with respect to time.

19. The method of claim 1, wherein at least one of the changes with respect to time is the first derivative of T wave amplitude with respect to timeand another of the changes with respect to time is the second derivative of T wave amplitude with respect to time.

20. The method of claim 1 in which said step of selecting T-wave shock times involves selection in relation to the minimum of the absolute value (zero point) of the second derivative of the T wave with respect to time.

21. The method of claim 1, further comprising the step of calculating a level of signal quality for the first derived signal and at least one second derived signal, and the one or more timing points are selected in relation to the calculated values of signal quality.

22. The method of claim 21, in which the level of signal quality is calculated using a pre-determined period of time and using a time-domain-based signal method selected from the group consisting of a minimum, a mean, a median, mode, and a maximum.

23. The method of claim 21, in which the level of signal quality is calculated using a pre-determined range of frequency and using a frequency-domain-based signal method selected from the group consisting of a minimum, a mean, a median, and a maximum signal value.

24. The method of claim 21, in which the level of signal quality is calculated using a method selected from the group consisting of an average signal difference, a sum of an absolute value of a difference from a signal mean and a power of a signal subtracted from a signal mean, a signal to noise ratio, a coefficient of signal variation, a signal histogram, a signal frequency spectrum, a signal power spectrum, a time-domain convolution technique, and a time-domain correlation technique.

25. The method of claim 21 in which the timing point is selected based on the derived signal with the highest quality.

26. The method of claim 21, in which, if more than one derived signal has sufficient quality, the priority in which such signals are used to select the timing point within the T-wave is specified in advance by predetermined instructions.

27. The method of claim 21, in which, if more than one derived signal has sufficient quality, the timing point for the T-wave shock is selected from a mathematical combination of the intervals from a predetermined base timing point to each of the timing points within the T-wave that can be determined with sufficient quality.

28. The method of claim 27, in which the mathematical combination is selected from the group consisting of an average, a weighted average, a median, and a mode.

29. The method of claim 27, wherein two changes with respect to time of each cardiac electrical signal are derived, the first change with respect to time being the first derivative of one cardiac electrical signal and the second change with respect to time being the second derivative of a different cardiac electrical signal.

30. The method of claim 21, further comprising the step of determining the signal with the highest quality from the set consisting of the base cardiac electrical signal and the one or more signals derived therefrom.

31. The method of claim 1 in which, if an extreme absolute value of the change with respect to time of one cardiac electrical signal occurs at more than one point in time, a timing point selected from one sensed cardiac electrical signal depends on the value of one or more other, different cardiac electrical signals, or of a change with respect to time of one or more other cardiac electrical signals.

32. The method of claim 31, in which a first timing point during the T wave for the test-shock is selected in relation to a maximum of a first derivative of the T wave with respect to time of one cardiac electrical signal and an at least one second timing point during the T wave is selected in relation to a minimum of an absolute value of a second derivative of the T wave with respect to time of the same cardiac electrical signal.

33. The method of claim 32, in which the minimum of the absolute value of the second derivative of the T wave with respect to time is a zero point.

34. The method of claims 33, and in which the zero point of the second derivative of the T wave with respect to time of the second cardiac electrical signal occurs when the first derivative of the same second cardiac electrical signal is not zero.

35. The method according to claim 33 or 34 in which:
(A) the maximum of the first derivative with respect to time of one cardiac electrical signal is used to select the timing point within the T wave only if the second derivative of the same cardiac electrical signal at the same point is a local minimum value, and
(B) otherwise, the minimum absolute value of the second derivative with respect to time of a different cardiac electrical signal is used to select the timing point within the T wave.

36. The method of claim 1, further comprising the step of recording the cardiac electrical signals from a fully implantable device.

37. The method of claims 1 in which the cardiac electrical signals are selected from a subset of cardiac electrical signals which are recorded from permanently implantable and non-implantable electrodes.

38. The method of claim 1 in which the cardiac electrical signals are selected from a subset of non-implantable electrodes and further comprising the step of transmitting the cardiac electrical signals wirelessly to an ICD programmer.

39. The method of claim 1 in which the cardiac electrical signals are selected from a subset of non-implantable electrodes and further comprising the step of transmitting the cardiac signals wirelessly to an ICD generator.

40. The method of claim 1 in which electrodes sense the cardiac electrical signals, the sensed signals being selected from a subset of cardiac electrical signals including but not limited to pacing, sensing, recording, and defibrillation electrodes.

41. The method of claims 1 in which electrodes sense the cardiac electrical signals, the sensed signals being selected from a subset of cardiac electrical signals including but not limited to subcutaneous electrodes, epicardial electrodes, transvenous endocardial electrodes, and transvenous endovascular electrodes.

42. The method of claims 1 in which electrodes sense the cardiac electrical signals, the sensed signals being selected from a subset of cardiac electrical signals including but not limited to a right ventricular pace-sense tip electrode, a right ventricular pace-sense ring electrode, a left ventricular pace-sense tip electrode, a left ventricular pace-sense ring electrode, a left atrial pace-sense tip electrode, a left atrial pace-sense ring electrode, a tip electrode placed in the coronary venous system, a ring electrode placed in the coronary venous system, a defibrillation electrode in the right ventricle, a defibrillation electrode in the left ventricle, a defibrillation electrode in the right atrium, a defibrillation electrode in the left atrium, an epicardial pace-sense electrode, an epicardial defibrillation electrode, a subcutaneous sensing electrode, a subcutaneous defibrillation electrode, a submuscular sensing electrode, a submuscular defibrillation electrode, a localized "button" electrode on the housing ("can") of an ICD pulse generator, an electrode consisting of the entire housing ("can") of the ICD pulse generator.

43. The method of claim 1 further comprising the step of determining a predetermined number of T-wave shocks by the quality of the cardiac electrical signal signals.

* * * * *